US008318425B2

(12) United States Patent
Salzwedel et al.

(10) Patent No.: US 8,318,425 B2
(45) Date of Patent: Nov. 27, 2012

(54) INHIBITION OF HIV-1 REPLICATION BY DISRUPTION OF THE PROCESSING OF THE VIRAL CAPSID-SPACER PEPTIDE 1 PROTEIN

(75) Inventors: Karl Salzwedel, Olney, MD (US); Feng Li, Brookings, SD (US); Carl T. Wild, Gaithersburg, MD (US); Graham P. Allaway, Darnestown, MD (US); Eric O. Freed, Frederick, MD (US)

(73) Assignees: The United States of America, as represented by the Secretary, Department & Human Services, Washington, DC (US); Myrexis, Inc., Salt Lake City, UT (US)

( * ) Notice: Subject to any disclaimer, the term of this patent is extended or adjusted under 35 U.S.C. 154(b) by 226 days.

(21) Appl. No.: 12/498,157

(22) Filed: Jul. 6, 2009

(65) Prior Publication Data

US 2010/0221264 A1    Sep. 2, 2010

Related U.S. Application Data

(63) Continuation of application No. 10/766,528, filed on Jan. 29, 2004, now abandoned.

(60) Provisional application No. 60/496,660, filed on Aug. 21, 2003, provisional application No. 60/443,180, filed on Jan. 29, 2003.

(51) Int. Cl.
| | |
|---|---|
| *C12Q 1/70* | (2006.01) |
| *C12Q 1/68* | (2006.01) |
| *A01N 61/00* | (2006.01) |
| *A01N 57/00* | (2006.01) |
| *A61K 31/00* | (2006.01) |
| *A61K 31/66* | (2006.01) |

(52) U.S. Cl. ........... 435/6.1; 435/5; 435/6.11; 435/6.12; 514/1; 514/120; 514/510

(58) Field of Classification Search ..................... None
See application file for complete search history.

(56) References Cited

U.S. PATENT DOCUMENTS 5,679,828 A * 10/1997 Lee et al. .............. 560/116

OTHER PUBLICATIONS

Hashimoto et al. Anti-AIDS agents—XXVII. Synthesis and Anti-HIV Activity of Betulinic Acid and Dihydrobetulinic Acid Derivatives. Bioorganic & Medicinal Chemistry 1997, vol. 5, No. 12, pp. 2133-2143.*
Huang et al. Bifunctional Anti-Human Immunodeficiency Virus Type 1 Small Molecules with Two Novel Mechanisms of Action. Antimicrobia Agents and Chemotherapy 2004, vol. 48, No. 2, p. 663-665.*
Sami et al. Pharmacological properties of the ubiquitous natural product betulin. European Journal of Pharmaceutical Sciences 2006, vol. 29, p. 1-13.*
Sakalian et al. 3-O-(3',3'-Dimethysuccinyl) Betulinic Acid Inhibits Maturation of the Human Immunodeficiency Virus Type 1 Gag Precursor Assembled in Vitro. Journal of Virology, Jun. 2006, vol. 80, No. 12, p. 5716-5722.*
Myers et al. Human Retroviruses and AIDS 1991. Los Alamos National Laboratory, Los Alamos, New Mexico 1991.*
Salminen et al. Recovery of Virtually Full-Length HIV-1 Provirus of Diverse Subtypes from Primary Virus Cultures Using the Polymerase Chain Reaction. Virology 1995, vol. 213, pp. 80-86.*

* cited by examiner

*Primary Examiner* — Louise Humphrey
(74) *Attorney, Agent, or Firm* — Edwards Wildman Palmer LLP; Peter F. Corless; Andrew W. Shyjan, Esq.

(57) ABSTRACT

Inhibition of HIV-1 replication by disrupting the processing of the viral Gag capsid (CA) protein (p24) from the CA-spacer peptide 1 (SP1) protein precursor (p25) is disclosed. Amino acid sequences containing a mutation in the Gag p25 protein, with the mutation resulting in a decrease in the inhibition of processing of p25 to p24 by dimethylsuccinyl betulinic acid or dimethylsuccinyl betulin, polynucleotides encoding such mutated sequences and antibodies that selectively bind such mutated sequences are also included. Methods of inhibiting, inhibitory compounds and methods of discovering inhibitory compounds that target proteolytic processing of the HIV Gag protein are included. In one embodiment, such compounds inhibit the interaction of the HIV protease enzyme with Gag by binding to the Gag proteolytic cleavage site rather than to the protease enzyme. In another embodiment, viruses or recombinant proteins that contain mutations in the region of the Gag proteolytic cleavage site can be used in screening assays to identify compounds that target proteolytic processing.

1 Claim, 11 Drawing Sheets

Gag sequence #1: K-A-R-V/I-L -|-A-E-A-M-S   (SEQ ID NO: 1)

Gag sequence #2: K-A-R-V-L-|-V-E-A-M-S   (SEQ ID NO: 2)

Gag sequence #3: K-A-R-I-L-|-A-E-V-M-S   (SEQ ID NO: 12)

FIGURE 5
(SEQ ID NO: 4)

ATGGGTGCGAGAGCGTCGGTATTAAGCGGGGGAGAATTAGATAAATGG
GAAAAAATTCGGTTAAGGCCAGGGGGAAAGAAACAATATAAACTAAAA
CATATAGTATGGGCAAGCAGGGAGCTAGAACGATTCGCAGTTAATCCT
GGCCTTTTAGAGACATCAGAAGGCTGTAGACAAATACTGGGACAGCTA
CAACCATCCCTTCAGACAGGATCAGAAGAACTTAGATCATTATATAAT
ACAATAGCAGTCCTCTATTGTGTGCATCAAAGGATAGATGTAAAAGAC
ACCAAGGAAGCCTTAGATAAGATAGAGGAAGAGCAAAACAAAAGTAAG
AAAAAGGCACAGCAAGCAGCAGCTGACACAGGAAACAACAGCCAGGTC
AGCCAAAATTACCCTATAGTGCAGAACCTCCAGGGGCAAATGGTACAT
CAGGCCATATCACCTAGAACTTTAAATGCATGGGTAAAAGTAGTAGAA
GAGAAGGCTTTCAGCCCAGAAGTAATACCCATGTTTTCAGCATTATCA
GAAGGAGCCACCCCACAAGATTTAAATACCATGCTAAACACAGTGGGG
GGACATCAAGCAGCCATGCAAATGTTAAAAGAGACCATCAATGAGGAA
GCTGCAGAATGGGATAGATTGCATCCAGTGCATGCAGGCCTATTGCA
CCAGGCCAGATGAGAGAACCAAGGGGAAGTGACATAGCAGGAACTACT
AGTACCCTTCAGGAACAAATAGGATGGATGACACATAATCCACCTATC
CCAGTAGGAGAAATCTATAAAAGATGGATAATCCTGGGATTAAATAAA
ATAGTAAGAATGTATAGCCCTACCAGCATTCTGGACATAAGACAAGGA
CCAAAGGAACCCTTTAGAGACTATGTAGACCGATTCTATAAAACTCTA
AGAGCCGAGCAAGCTTCACAAGAGGTAAAAAATTGGATGACAGAAACC
TTGTTGGTCCAAAATGCGAACCCAGATTGTAAGACTATTTTAAAAGCA
TTGGGACCAGGAGCGACACTAGAAGAAATGATGACAGCATGTCAGGGA
GTGGGGGGACCCGGCCATAAAGCAAGAGTTTTGGTTGAAGCAATGAGC
CAAGTAACAAATCCAGCTACCATAATGATACAGAAAGGCAATTTTAGG
AACCAAAGAAAGACTGTTAAGTGTTTCAATTGTGGCAAAGAAGGGCAC
ATAGCCAAAAATTGCAGGGCCCCTAGGAAAAAGGGCTGTTGGAAATGT
GGAAAGGAAGGACACCAAATGAAAGATTGTACTGAGAGACAGGCTAAT
TTTTTAGGGAAGATCTGGCCTTCCCACAAGGGAAGGCCAGGGAATTTT
CTTCAGAGCAGACCAGAGCCNACAGCCCCACCAGAAGAGAGCTTCAGG
TTTGGGGAAGAGACAACAACTCCCTCTCAGAAGCAGGAGCCGATAGAC
AAGGAACTGTATCCTTTAGCTTCCCTCAGATCACTCTTTGGCAGCGAC
CCCTCGTCACAATAAAGATAGGGGGGCAATTAAAGGAAGCTCTATTAG
ATACAGGAGCAGATGATACAGTATTAGAAGAAATGAATTTGCCAGGAA
GATGGAAACCAAAAATGATAGGGGGAATTGGAGGTTTTATCAAAGTAA
GACAGTATGATCAGATACTCATAGAAATCTGCGGACATAAAGCTATAG
GTACAGTATTAGTAGGACCTACACCTGTCAACATAATTGGAAGAAATC
TGTTGACTCAGATTGGCTGCACTTTAAATTTTCCCATTAGTCCTATTG
AGACTGTACCAGTAAAATTAAAGCCAGGAATGGATGGCCCAAAAGTT

FIGURE 6
(SEQ ID NO: 5)

ATGGGTGCGAGAGCGTCGGTATTAAGCGGGGGAGAATTAGATAAATGG
GAAAAAATTCGGTTAAGGCCAGGGGGAAAGAAACAATATAAACTAAAA
CATATAGTATGGGCAAGCAGGGAGCTAGAACGATTCGCAGTTAATCCT
GGCCTTTTAGAGACATCAGAAGGCTGTAGACAAATACTGGGACAGCTA
CAACCATCCCTTCAGACAGGATCAGAAGAACTTAGATCATTATATAAT
ACAATAGCAGTCCTCTATTGTGTGCATCAAAGGATAGATGTAAAAGAC
ACCAAGGAAGCCTTAGATAAGATAGAGGAAGAGCAAAACAAAAGTAAG
AAAAAGGCACAGCAAGCAGCAGCTGACACAGGAAACAACAGCCAGGTC
AGCCAAAATTACCCTATAGTGCAGAACCTCCAGGGGCAAATGGTACAT
CAGGCCATATCACCTAGAACTTTAAATGCATGGGTAAAAGTAGTAGAA
GAGAAGGCTTTCAGCCCAGAAGTAATACCCATGTTTTCAGCATTATCA
GAAGGAGCCACCCCACAAGATTTAAATACCATGCTAAACACAGTGGGG
GGACATCAAGCAGCCATGCAAATGTTAAAAGAGACCATCAATGAGGAA
GCTGCAGAATGGGATAGATTGCATCCAGTGCAGGCAGGCCTATTGCA
CCAGGCCAGATGAGAGAACCAAGGGGAAGTGACATAGCAGGAACTACT
AGTACCCTTCAGGAACAAATAGGATGGATGACACATAATCCACCTATC
CCAGTAGGAGAAATCTATAAAAGATGGATAATCCTGGGATTAAATAAA
ATAGTAAGAATGTATAGCCCTACCAGCATTCTGGACATAAGACAAGGA
CCAAAGGAACCCTTTAGAGACTATGTAGACCGATTCTATAAAACTCTA
AGAGCCGAGCAAGCTTCACAAGAGGTAAAAAATTGGATGACAGAAACC
TTGTTGGTCCAAAATGCGAACCCAGATTGTAAGACTATTTTAAAAGCA
TTGGGACCAGGAGCGACACTAGAAGAAATGATGACAGCATGTCAGGGA
GTGGGGGGACCCGGCCATAAAGCAAGAGTTTTGGCTGAAGCAATGAGC
CAAGTAACAAATCCAGCTACCATAATGATACAGAAAGGCAATTTTAGG
AACCAAAGAAAGACTGTTAAGTGTTTCAATTGTGGCAAAGAAGGGCAC
ATAGCCAAAAATTGCAGGGCCCCTAGGAAAAAGGGCTGTTGGAAATGT
GGAAAGGAAGGACACCAAATGAAAGATTGTACTGAGAGACAGGCTAAT
TTTTTAGGGAAGATCTGGCCTTCCCACAAGGGAAGGCCAGGGAATTTT
CTTCAGAGCAGACCAGAGCCAACAGCCCCACCAGAAGAGAGCTTCAGG
TTTGGGGAAGAGACAACAACTCCCTCTCAGAAGCAGGAGCCGATAGAC
AAGGAACTGTATCCTTTAGCTTCCTCAGATCACTCTTTGGCAGCGAC
CCCTCGTCACAATAAAGATAGGGGGGCAATTAAAGGAAGCTCTATTAG
ATACAGGAGCAGATGATACAGTATTAGAAGAAATGAATTTGCCAGGAA
GATGGAAACCAAAAATGATAGGGGAATTGGAGGTTTTATCAAAGTAA
GACAGTATGATCAGATACTCATAGAAATCTGCGGACATAAAGCTATAG
GTACAGTATTAGTAGGACCTACACCTGTCAACATAATTGGAAGAAATC
TGTTGACTCAGATTGGCTGCACTTTAAATTTTCCCATTAGTCCTATTG
AGACTGTACCAGTAAAATTAAAGCCAGGAATGGATGGCCCAAAG

FIGURE 7A
(SEQ ID NO: 6)

ATGGGTGCGAGAGCGTCAGTATTAAGCGGCGGAAAATTAGACAAATGG
GAAAAAATTCGGTTAAGGCCAGGGGGAAAGAAAAGATATAAGTTAAAA
CATATAATATGGGCAAGCAGGGAGCTAGAACGATTTGCTGTCAATCCT
GGCCTTTTAGAGACAGCAGAGGGCTGTAGACAAATACTGGGACAGCTA
CAACCAGCCCTTCAGACAGGATCAGAAGAACTTAAATCATTATATAAT
GCAGTAGCAACCCTCTATTGTGTACATCAAAATATAGAGGTAAGAGAC
ACCAAGGAAGCTTTAGACAAGATAGAGGAAGAGCAAAACAAAAGTAAG
AAAAAAGCACAGCAAGCAGCAGCTGACACAGGAAACGGCAGCCAGGTC
AGCCAAAATTACCCTATAGTGCAGAACCTTCAGGGGCAAATGGTACAT
CAAGCCATATCACCTAGAACTTTAAATGCATGGGTAAAAGTAGTAGAA
GAGAAGGCTTTTAGCCCAGAAGTAATACCCATGTTTTCAGCATTATCA
GAAGGAGCCACCCCACAAGATTTAAACACCATGCTAAACACAGTGGGG
GGACATCAAGCAGCCATGCAAATGTTAAAAGAGACTATCAATGAGGAA
GCTGCAGAATGGGATAGATTGCATCCAGTGCAAGCAGGGCCTATTGCA
CCAGGCCAGATGAGAGAACCAAGGGGAAGTGACATAGCAGGAACCACT
AGTACCCTTCAGGAACAAATAGGATGGATGACAAATAATCCACCTATC
CCAGTAGGAGAAATCTATAAAAGGTGGATAATTCTGGGATTAAATAAA
ATAGTAAGAATGTATAGCCCCATCAGCATTCTGGACATAAGACAAGGA
CCTAAGGAACCCTTTAGAGACTATGTAGACCGGTTCTATAAAACTCTA
AGAGCCGAGCAAGCTTCACAGGATGTAAAAAATTGGATGACAGAAACC
TTGCTGGTCCAAAATGCGAACCCAGATTGTAAAACTATTTTAAAAGCA
TTGGGACCAGCAGCTACACTAGAAGAAATGATGACAGCATGTCAGGGA
GTAGGGGGACCCAGCCATAAAGCAAGAATTTTGCTGAAGTAATGAGC
CAAGTAACAAATTCAGCTACCATAATGCTGCAGAAAGGTAATTTTAGG
GACCAAAGAAAAATTGTTAAGTGTTTCAACTGTGGCAAAGTAGGGCAC
ATAGCCAAAAATTGCAGGGCCCCTAGGAAAAAGGGCTGTTGGAAATGT
GGAAAGGAAGGACACCAAATGAAAGATTGCACTACTGAGGGACGACAG
GCTAATTTTTTAGGGAAAATCTGGCCTTCCCACAAGGGAAGGCCAGGG
AACTTTCTTCAGAGCAGACCAGAGCCAACAGCCCCACCAGAAGAGAGC
TTCAGGTTTGGGGAAGAGACAACTCCCTCTCAGAAGCAGGAGAAGATA
GACAAGGAACTGTATCCTTTAGCTTCCCTCAAATCACTCTTTGGCAAC
GACCCATCGTCACAGTAAAGATAGGGGGGCAATTAAAGGAAGCTCTAT
TAGATACAGGAGCAGATGATACAGTATTAGAAGAAATGAATTTGCCAG
GAAAATGGAAACCAAAAATGATAGGGGGAATTGGAGGTTTTATCAAAG
TAAGGCAGTATGATCAAATACTCATAGAAATCTGTGGACATAAAGCTA
TAGGTACAGTATTAGTAGGACCTACACCTGTCAACATAATTGGAAGAA
ATCTGTTGACTCAGATTGGTTGCACTTTAAATTTTCCCATTAGTCCTA
TTGAAACTATACCAGTAAAATTAAAGCCAGGAATGGATGGCCCAAAAG
TTAAACAATGGCCATTGACAGAGGAAAAAATAAAAGCATTGATAGAAA
TTTGTACAGAAATGGAAAAGGAAGGAAAAATTTCAAAAATTGGGCCTG

FIGURE 7B

AAAATCCATACAATACTCCAGTATTTGCCATAAAGAAAAANGACAGTA
CTAAATGGAGAAAA

FIGURE 8

(SEQ ID NO: 7)

ATGGGTGCGAGAGCGTCAGTATTAAGCGGCGGAAAATTAGACAAATGG
GAAAAAATTCGGTTAAGGCCAGGGGGAAAGAAAAGATATAAGTTAAAA
CATATAATATGGGCAAGCAGGGAGCTAGAACGATTTGCTGTCAATCCT
GGCCTTTTAGAGACAGCAGAGGGCTGTAGACAAATACTGGGACAGCTA
CAACCAGCCCTTCAGACAGGATCAGAAGAACTTAAATCATTATATAAT
GCAGTAGCAACCCTCTATTGTGTACATCAAAATATAGAGGTAAGAGAC
ACCAAGGAAGCTTTAGACAAGATAGAGGAAGAGCAAAACAAAAGTAAG
AAAAAAGCACAGCAAGCAGCAGCTGACACAGGAAACGGCAGCCAGGTC
AGCCAAAATTACCCTATAGTGCAGAACCTTCAGGGGCAAATGGTACAT
CAAGCCATATCACCTAGAACTTTAAATGCATGGGTAAAAGTAGTAGAA
GAGAAGGCTTTTAGCCCAGAAGTAATACCCATGTTTTCAGCATTATCA
GAAGGAGCCACCCCACAAGATTTAAACACCATGCTAAACACAGTGGGG
GGACATCAAGCAGCCATGCAAATGTTAAAAGAGACTATCAATGAGGAA
GCTGCAGAATGGGATAGATTGCATCCAGTGCAAGCAGGGCCTATTGCA
CCAGGCCAGATGAGAGAACCAAGGGGAAGTGACATAGCAGGAACCACT
AGTACCCTTCAGGAACAAATAGGATGGATGACAAATAATCCACCTATC
CCAGTAGGAGAAATCTATAAAAGGTGGATAATTCTGGGATTAAATAAA
ATAGTAAGAATGTATAGCCCCATCAGCATTCTGGACATAAGACAAGGA
CCTAAGGAACCCTTTAGAGACTATGTAGACCGGTTCTATAAAACTCTA
AGAGCCGAGCAAGCTTCACAGGATGTAAAAAATTGGATGACAGAAACC
TTGCTGGTCCAAAATGCGAACCCAGATTGTAAAACTATTTTAAAAGCA
TTGGGACCAGCAGCTACACTAGAAGAAATGATGACAGCATGTCAGGGA
GTAGGGGACCCAGCCATAAAGCAAGAATTTTGGCTGAAGCAATGAGC
CAAGTAACAAATTCAGCTACCATAATGCTGCAGAAAGGTAATTTTAGG
GACCAAAGAAAAATTGTTAAGTGTTTCAACTGTGGCAAAGTAGGGCAC
ATAGCCAAAAATTGCAGGGCCCCTAGGAAAAAGGGCTGTTGGAAATGT
GGAAAGGAAGGACACCAAATGAAAGATTGCACTACTGAGGGACGACAG
GCTAATTTTTTAGGGAAAATCTGGCCTTCCCACAAGGGAAGGCCAGGG
AACTTTCTTCAGAGCAGACCAGAGCCAACAGCCCCACCAGAAGAGAGC
TTCAGGTTTGGGGAAGAGACAACTCCCTCTCAGAAGCAGGAGAAGATA
GACAAGGAACTGTATCCTTTAGCTTCCCTCAAATCACTCTTTGGCAAC
GACCCATCGTCACAGTAAAGATAGGGGGCAATTAAAGGAAGCTCTAT
TAGATACAGGAGCAGATGATACAGTATTAGAAGAAATGAATTTGCCAG
GAAAATGGAAACCAAAATGATAGGGGGAATTGGAGGTTTTATCAAAG
TAAGGCAGTATGATCAAATACTCATAGAAATCTGTGGACATAAAGCTA
TAGGTACAGTATTAGTAGGACCTACACCTGTCAACATAATTGGAAGAA
ATCTGTTGACTCAGATTGGTTGCACTTTAAATTTTCCCATTAGTCCTA
TTGAAACTATACCAGTAAAATTAAAGCCAGGAATGGATGGCCCAAAAG
TTAAACAATGGCCATTGACAGAGGAAAAAATAAAAGCATTGATAGAAA
TTTGTACAGAAATGGAAAAGGAAGGAAAAATT

FIGURE 9

AAAGCAAGAGTTTTGGTTGAAGCAATGAGC    (SEQ ID NO: 8)

AAAGCAAGAATTTTGGCTGAAGTAATGAGC    (SEQ ID NO: 9)

AAAGCAAGAA/GTTTTGGCTGAAGCAATGAGC    (SEQ ID NO: 10)

K-A-R-L-M-|-A̲-E-A̲-L-K  (SEQ ID NO: 11)

SEQUENCE LISTING

```
<160> NUMBER OF SEQ ID NOS: 12

<210> SEQ ID NO 1
<211> LENGTH: 10
<212> TYPE: PRT
<213> ORGANISM: Human immunodeficiency virus type 1
<220> FEATURE:
<221> NAME/KEY: MOD_RES
<222> LOCATION: (5)..(5)
<223> OTHER INFORMATION: Leu or Ile

<400> SEQUENCE: 1

Lys Ala Arg Val Xaa Ala Glu Ala Met Ser
1               5                   10

<210> SEQ ID NO 2
<211> LENGTH: 10
<212> TYPE: PRT
<213> ORGANISM: Human immunodeficiency virus type 1

<400> SEQUENCE: 2

Lys Ala Arg Val Leu Val Glu Ala Met Ser
1               5                   10

<210> SEQ ID NO 3
<211> LENGTH: 10
<212> TYPE: PRT
<213> ORGANISM: Human immunodeficiency virus type 1

<400> SEQUENCE: 3

Lys Ala Arg Ile Leu Ala Glu Val Met Ser
1               5                   10

<210> SEQ ID NO 4
<211> LENGTH: 1823
<212> TYPE: DNA
<213> ORGANISM: Artificial Sequence
<220> FEATURE:
<223> OTHER INFORMATION: Description of Artificial Sequence: Synthetic
      consensus sequence
<220> FEATURE:
<221> NAME/KEY: modified_base
<222> LOCATION: (1365)..(1365)
<223> OTHER INFORMATION: a, c, t, g, unknown or other

<400> SEQUENCE: 4
atgggtgcga gagcgtcggt attaagcggg ggagaattag ataaatggga aaaaattcgg      60
ttaaggccag ggggaaagaa acaatataaa ctaaaacata tagtatgggc aagcagggag     120
ctagaacgat tcgcagttaa tcctggcctt ttagagacat cagaaggctg tagacaaata     180
ctgggacagc tacaaccatc ccttcagaca ggatcagaag aacttagatc attatataat     240
acaatagcag tcctctattg tgtgcatcaa aggatagatg taaaagacac caaggaagcc     300
ttagataaga tagaggaaga gcaaaacaaa agtaagaaaa aggcacagca agcagcagct     360
gacacaggaa acaacagcca ggtcagccaa aattacccta tagtgcagaa cctccagggg     420
caaatggtac atcaggccat atcacctaga actttaaatg catgggtaaa agtagtagaa     480
gagaaggctt tcagcccaga agtaataccc atgttttcag cattatcaga aggagccacc     540
```

| | |
|---|---|
| ccacaagatt taaataccat gctaaacaca gtgggggggac atcaagcagc catgcaaatg | 600 |
| ttaaaagaga ccatcaatga ggaagctgca gaatgggata gattgcatcc agtgcatgca | 660 |
| gggcctattg caccaggcca gatgagagaa ccaaggggaa gtgacatagc aggaactact | 720 |
| agtacccttc aggaacaaat aggatggatg acacataatc cacctatccc agtaggagaa | 780 |
| atctataaaa gatggataat cctgggatta aataaaatag taagaatgta tagccctacc | 840 |
| agcattctgg acataagaca aggaccaaag gaacccttta gagactatgt agaccgattc | 900 |
| tataaaactc taagagccga gcaagcttca caagaggtaa aaaattggat gacagaaacc | 960 |
| ttgttggtcc aaaatgcgaa cccagattgt aagactattt taaaagcatt gggaccagga | 1020 |
| gcgacactag aagaaatgat gacagcatgt cagggagtgg ggggacccgg ccataaagca | 1080 |
| agagttttgg ttgaagcaat gagccaagta acaaatccag ctaccataat gatacagaaa | 1140 |
| ggcaatttta ggaaccaaag aaagactgtt aagtgtttca attgtggcaa agaagggcac | 1200 |
| atagccaaaa attgcagggc ccctaggaaa aagggctgtt ggaaatgtgg aaggaagga | 1260 |
| caccaaatga agattgtac tgagagacag gctaattttt tagggaagat ctggccttcc | 1320 |
| cacaagggaa ggccagggaa ttttcttcag agcagaccag agccnacagc cccaccagaa | 1380 |
| gagagcttca ggtttgggga agagacaaca actccctctc agaagcagga gccgatagac | 1440 |
| aaggaactgt atcctttagc ttccctcaga tcactctttg gcagcgaccc ctcgtcacaa | 1500 |
| taaagatagg gggcaatta aaggaagctc tattagatac aggagcagat gatacagtat | 1560 |
| tagaagaaat gaatttgcca ggaagatgga accaaaaat gatagggga attggaggtt | 1620 |
| ttatcaaagt aagacagtat gatcagatac tcatagaaat ctgcggacat aaagctatag | 1680 |
| gtacagtatt agtaggacct acacctgtca acataattgg aagaaatctg ttgactcaga | 1740 |
| ttggctgcac tttaaatttt cccattagtc ctattgagac tgtaccagta aaattaaagc | 1800 |
| caggaatgga tggcccaaaa gtt | 1823 |

<210> SEQ ID NO 5
<211> LENGTH: 1820
<212> TYPE: DNA
<213> ORGANISM: Artificial Sequence
<220> FEATURE:
<223> OTHER INFORMATION: Description of Artificial Sequence: Synthetic consensus sequence

<400> SEQUENCE: 5

| | |
|---|---|
| atgggtgcga gagcgtcggt attaagcggg ggagaattag ataaatggga aaaaattcgg | 60 |
| ttaaggccag ggggaaagaa acaatataaa ctaaaacata tagtatgggc aagcagggag | 120 |
| ctagaacgat tcgcagttaa tcctggcctt ttagagacat cagaaggctg tagacaaata | 180 |
| ctgggacagc tacaaccatc ccttcagaca ggatcagaag aacttagatc attatataat | 240 |
| acaatagcag tcctctattg tgtgcatcaa aggatagatg taaaagacac caaggaagcc | 300 |
| ttagataaga tagaggaaga gcaaaacaaa agtaagaaaa aggcacagca agcagcagct | 360 |
| gacacaggaa acaacagcca ggtcagccaa aattacccta gtgtcagaa cctccagggg | 420 |
| caaatggtac atcaggccat atcacctaga actttaaatg catgggtaaa agtagtagaa | 480 |
| gagaaggctt tcagcccaga agtaataccc atgttttcag cattatcaga aggagccacc | 540 |
| ccacaagatt taaataccat gctaaacaca gtgggggggac atcaagcagc catgcaaatg | 600 |
| ttaaaagaga ccatcaatga ggaagctgca gaatgggata gattgcatcc agtgcaggca | 660 |
| gggcctattg caccaggcca gatgagagaa ccaaggggaa gtgacatagc aggaactact | 720 |

```
agtacccttc aggaacaaat aggatggatg acacataatc cacctatccc agtaggagaa       780
atctataaaa gatggataat cctgggatta aataaaatag taagaatgta tagccctacc       840
agcattctgg acataagaca aggaccaaag gaacccttta gagactatgt agaccgattc       900
tataaaactc taagagccga gcaagcttca caagaggtaa aaaattggat gacagaaacc       960
ttgttggtcc aaaatgcgaa cccagattgt aagactattt taaaagcatt gggaccagga      1020
gcgacactag aagaaatgat gacagcatgt cagggagtgg ggggacccgg ccataaagca      1080
agagttttgg ctgaagcaat gagccaagta acaaatccag ctaccataat gatacagaaa      1140
ggcaatttta ggaaccaaag aaagactgtt aagtgtttca attgtggcaa agaagggcac      1200
atagccaaaa attgcagggc ccctaggaaa aagggctgtt ggaaatgtgg aaaggaagga      1260
caccaaatga agattgtac tgagagacag gctaattttt tagggaagat ctggccttcc       1320
cacaagggaa ggccagggaa ttttcttcag agcagaccag agccaacagc cccaccagaa      1380
gagagcttca ggtttgggga agagacaaca actccctctc agaagcagga gccgatagac      1440
aaggaactgt atcctttagc ttccctcaga tcactctttg gcagcgaccc ctcgtcacaa      1500
taaagatagg ggggcaatta aaggaagctc tattagatac aggagcagat gatacagtat      1560
tagaagaaat gaatttgcca ggaagatgga accaaaaat gatagggga attggaggtt        1620 ttatcaaagt aagacagtat gatcagatac tcatagaaat ctgcggacat aaagctatag      1680
gtacagtatt agtaggacct acacctgtca acataattgg aagaaatctg ttgactcaga      1740
ttggctgcac tttaaatttt cccattagtc ctattgagac tgtaccagta aaattaaagc      1800
caggaatgga tggcccaaag                                                  1820
```

<210> SEQ ID NO 6
<211> LENGTH: 1982
<212> TYPE: DNA
<213> ORGANISM: Artificial Sequence
<220> FEATURE:
<223> OTHER INFORMATION: Description of Artificial Sequence: Synthetic consensus sequence
<220> FEATURE:
<221> NAME/KEY: modified_base
<222> LOCATION: (1961)..(1961)
<223> OTHER INFORMATION: a, c, t, g, unknown or other

<400> SEQUENCE: 6

```
atgggtgcga gagcgtcagt attaagcggc ggaaaattag acaaatggga aaaaattcgg        60
ttaaggccag ggggaaagaa aagatataag ttaaaacata atatatggca agcaggggag       120
ctagaacgat ttgctgtcaa tcctggcctt ttagagacag cagagggctg tagacaaata       180
ctgggacagc tacaaccagc ccttcagaca ggatcagaag aacttaaatc attatataat       240
gcagtagcaa ccctctattg tgtacatcaa aatatagagg taagagacac caaggaagct       300
ttagacaaga tagaggaaga gcaaaacaaa agtaagaaaa agcacagca agcagcagct       360 gacacaggaa acggcagcca ggtcagccaa aattacccta gtgcagaa ccttcagggg        420 caaatggtac atcaagccat atcacctaga actttaaatg catgggtaaa agtagtagaa      480
gagaaggctt ttagcccaga agtaataccc atgttttcag cattatcaga aggagccacc      540
ccacaagatt taaacaccat gctaaacaca gtgggggggac atcaagcagc catgcaaatg      600
ttaaaagaga ctatcaatga ggaagctgca gaatgggata gattgcatcc agtgcaagca      660
gggcctattg caccaggcca gatgagagaa ccaaggggaa gtgacatagc aggaaccact      720
agtacccttc aggaacaaat aggatggatg acaaataatc cacctatccc agtaggagaa      780
atctataaaa ggtggataat cctgggatta aataaaatag taagaatgta tagccccatc      840
```

```
agcattctgg acataagaca aggacctaag gaacccttta gagactatgt agaccggttc    900
tataaaactc taagagccga gcaagcttca caggatgtaa aaaattggat gacagaaacc    960
ttgctggtcc aaaatgcgaa cccagattgt aaaactattt taaaagcatt gggaccagca   1020
gctacactag aagaaatgat gacagcatgt cagggagtag ggggacccag ccataaagca   1080
agaatttttgg ctgaagtaat gagccaagta acaaattcag ctaccataat gctgcagaaa  1140
ggtaatttta gggaccaaag aaaaattgtt aagtgtttca actgtggcaa agtagggcac   1200
atagccaaaa attgcagggc ccctaggaaa aagggctgtt ggaaatgtgg aaaggaagga   1260
caccaaatga aagattgcac tactgaggga cgacaggcta atttttagg gaaaatctgg    1320
ccttcccaca agggaaggcc agggaacttt cttcagagca gaccagagcc aacagcccca   1380
ccagaagaga gcttcaggtt tggggaagag acaactccct ctcagaagca ggagaagata   1440
gacaaggaac tgtatccttt agcttccctc aaatcactct ttggcaacga cccatcgtca   1500
cagtaaagat agggggggcaa ttaaggaag ctctattaga tacaggagca gatgatacag   1560
tattagaaga aatgaatttg ccaggaaaat ggaaaccaaa aatgataggg ggaattggag   1620
gttttatcaa agtaaggcag tatgatcaaa tactcataga aatctgtgga cataaagcta   1680
taggtacagt attagtagga cctacacctg tcaacataat tggaagaaat ctgttgactc   1740
agattggttg cactttaaat tttcccatta gtcctattga aactatacca gtaaaattaa   1800
agccaggaat ggatggccca aaagttaaac aatggccatt gacagaggaa aaaataaaag   1860
cattgataga aatttgtaca gaaatggaaa aggaaggaaa aatttcaaaa attgggcctg   1920
aaaatccata caatactcca gtatttgcca taagaaaaa ngacagtact aaatgggagaa  1980
aa                                                                 1982

<210> SEQ ID NO 7
<211> LENGTH: 1904
<212> TYPE: DNA
<213> ORGANISM: Artificial Sequence
<220> FEATURE:
<223> OTHER INFORMATION: Description of Artificial Sequence: Synthetic
      consensus sequence

<400> SEQUENCE: 7
atgggtgcga gagcgtcagt attaagcggc ggaaaattag acaaatggga aaaaattcgg     60
ttaaggccag ggggaaagaa aagatataag ttaaaacata atatgggc aagcagggag     120
ctagaacgat tgctgtgtcaa tcctggcctt tagagacag cagagggctg tagacaaata    180
ctgggacagc tacaaccagc ccttcagaca ggatcagaag aacttaaatc attatataat    240
gcagtagcaa ccctctattg tgtacatcaa aatatagagg taagagacac caaggaagct    300
ttagacaaga tagaggaaga gcaaaacaaa agtaagaaaa aagcacagca agcagcagct    360
gacacaggaa acgcagcca ggtcagccaa aattacccta gtgcagaa ccttcagggg      420
caaatggtac atcaagccat atcacctaga actttaaatg catgggtaaa agtagtagaa    480
gagaaggctt ttagcccaga agtaataccc atgttttcag cattatcaga aggagccacc    540
ccacaagatt taaacaccat gctaaacaca gtggggggac atcaagcagc catgcaaatg    600
ttaaaagaga ctatcaatga ggaagctgca gaatgggata gattgcatcc agtgcaagca    660
gggcctattg caccaggcca gatgagagaa ccaaggggaa gtgacatagc aggaaccact    720
agtacccttc aggaacaaat aggatggatg acaaataatc cacctatccc agtaggagaa    780
atctataaaa ggtggataat tctgggatta aataaaatag taagaatgta tagccccatc    840
```

```
agcattctgg acataagaca aggacctaag gaacccttta gagactatgt agaccggttc    900
tataaaactc taagagccga gcaagcttca caggatgtaa aaaattggat gacagaaacc    960
ttgctggtcc aaaatgcgaa cccagattgt aaaactattt taaaagcatt gggaccagca   1020
gctacactag aagaaatgat gacagcatgt cagggagtag ggggacccag ccataaagca   1080
agaattttgg ctgaagcaat gagccaagta acaaattcag ctaccataat gctgcagaaa   1140 ggtaattttta gggaccaaag aaaaattgtt aagtgtttca actgtggcaa agtagggcac   1200
atagccaaaa attgcagggc ccctaggaaa aagggctgtt ggaaatgtgg aaggaagga   1260 caccaaatga agattgcac tactgaggga cgacaggcta attttttagg gaaaatctgg   1320
ccttcccaca agggaaggcc agggaacttt cttcagagca gaccagagcc aacagcccca   1380
ccagaagaga gcttcaggtt tggggaagag acaactccct ctcagaagca ggagaagata   1440
gacaaggaac tgtatccttt agcttccctc aaatcactct ttggcaacga cccatcgtca   1500
cagtaaagat aggggggcaa ttaaggaag ctctattaga tacaggagca gatgatacag   1560
tattagaaga aatgaatttg ccaggaaaat ggaaaccaaa aatgataggg ggaattggag   1620
gttttatcaa agtaaggcag tatgatcaaa tactcataga aatctgtgga cataaagcta   1680
taggtacagt attagtagga cctacacctg tcaacataat tggaagaaat ctgttgactc   1740
agattggttg cactttaaat tttcccatta gtcctattga aactatacca gtaaaattaa   1800
agccaggaat ggatggccca aaagttaaac aatggccatt gacagaggaa aaaataaaag   1860
cattgataga aatttgtaca gaaatggaaa aggaaggaaa aatt              1904

<210> SEQ ID NO 8
<211> LENGTH: 30
<212> TYPE: DNA
<213> ORGANISM: Human immunodeficiency virus type 1

<400> SEQUENCE: 8
aaagcaagag ttttggttga agcaatgagc                                      30

<210> SEQ ID NO 9
<211> LENGTH: 30
<212> TYPE: DNA
<213> ORGANISM: Human immunodeficiency virus type 1

<400> SEQUENCE: 9
aaagcaagaa ttttggctga agtaatgagc                                      30

<210> SEQ ID NO 10
<211> LENGTH: 30
<212> TYPE: DNA
<213> ORGANISM: Human immunodeficiency virus type 1

<400> SEQUENCE: 10
aaagcaagag ttttggctga agcaatgagc                                      30

<210> SEQ ID NO 11
<211> LENGTH: 10
<212> TYPE: PRT
<213> ORGANISM: Human immunodeficiency virus type 1

<400> SEQUENCE: 11

Lys Ala Arg Leu Met Ala Glu Ala Leu Lys
1               5                   10

<210> SEQ ID NO 12
<211> LENGTH: 10
```

-continued

```
<212> TYPE: PRT
<213> ORGANISM: Human immunodeficiency virus type 1

<400> SEQUENCE: 12

Lys Ala Arg Val Ile Ala Glu Val Met Ser
1               5                   10
```

INHIBITION OF HIV-1 REPLICATION BY DISRUPTION OF THE PROCESSING OF THE VIRAL CAPSID-SPACER PEPTIDE 1 PROTEIN

This application is a continuation of U.S. application Ser. No. 10/766,528, filed Jan. 29, 2004, which is abandoned, which claims the benefit of U.S. Provisional Application Nos. 60/496,660, filed Aug. 21, 2003, and 60/443,180, filed Jan. 29, 2003, each of which is herein incorporated by reference.

STATEMENT REGARDING FEDERALLY-SPONSORED RESEARCH AND DEVELOPMENT

The U.S. Government has a paid-up license in this invention and the right in limited circumstances to require the patent owner to license others on reasonable terms as provided for by the terms of Grant No. 2R44AI051047-02 awarded by NIH/NIAID.

The instant application contains a Sequence Listing which has been submitted via EFS-Web and is hereby incorporated by reference in its entirety. Said ASCII copy, created on May 17, 2010, is named 86376CON.txt, and is 12,739 bytes in size.

BACKGROUND OF THE INVENTION

1. Field of the Invention

The invention includes methods of inhibiting, inhibitors and methods of discovery of inhibitors of HIV infection.

2. Background

Human Immunodeficiency Virus (HIV) is a member of the lentiviruses, a subfamily of retroviruses. Many retroviruses are well-known carcinogens. HIV per se is not known to cause cancer in humans or other animals, but it does present a formidable challenge to the host. The viral genome contains many regulatory elements which allow the virus to control its rate of replication in both resting and dividing cells. Most importantly, HIV infects and invades cells of the immune system; it breaks down the body's immune system and renders the patient susceptible to opportunistic infections and neoplasms. The immune defect appears to be progressive and irreversible, with a high mortality rate that approaches 100% over several years.

HIV-1 is trophic and cytopathic for T4 lymphocytes, cells of the immune system which express the cell surface differentiation antigen CD4, also known as OKT4, T4 and leu3. The viral tropism is due to the interactions between the viral envelope glycoprotein, gp120, and the cell-surface CD4 molecules (Dalgleish et al., Nature 312:763-767 (1984)). These interactions not only mediate the infection of susceptible cells by HIV, but are also responsible for the virus-induced fusion of infected and uninfected T cells. This cell fusion results in the formation of giant multinucleated syncytia, cell death, and progressive depletion of CD4 cells in HIV-infected patients. These events result in HIV-induced immunosuppression and its subsequent sequelae, opportunistic infections and neoplasms.

In addition to CD4+ T cells, the host range of HIV includes cells of the mononuclear phagocytic lineage (Dalgleish et al., supra), including blood monocytes, tissue macrophages, Langerhans cells of the skin and dendritic reticulum cells within lymph nodes. HIV is also neurotropic, capable of infecting monocytes and macrophages in the central nervous system causing severe neurologic damage. Macrophage and monocytes are major reservoirs of HIV. They can interact and fuse with CD4-bearing T cells, causing T cell depletion and thus contributing to the pathogenesis of AIDS.

Considerable progress has been made in the development of drugs for HIV-1 therapy. Therapeutic agents for HIV can include, but are not limited to, at least one of AZT, 3TC, ddC, d4T, ddI, tenofovir, abacavir, nevirapine, delavirdine, efavirenz, saquinavir, ritonavir, indinavir, nelfinavir, lopinavir and amprenavir, or any other antiretroviral drugs or antibodies in combination with each other, or associated with a biologically based therapeutic, such as, for example, gp41-derived peptides enfuvirtide (Fuzeon; Timeris-Roche) and T-1249 (Trimeris), or soluble CD4, antibodies to CD4, and conjugates of CD4 or anti-CD4, or as additionally presented herein. Combinations of these drugs are particularly effective and can reduce levels of viral RNA to undetectable levels in the plasma and slow the development of viral resistance, with resulting improvements in patient health and life span.

Despite these advances, there are still problems with the currently available drug regimens. Many of the drugs exhibit severe toxicities, have other side-effects (e.g., fat redistribution) or require complicated dosing schedules that reduce compliance and thereby limit efficacy. Resistant strains of HIV often appear over extended periods of time even on combination therapy. The high cost of these drugs is also a limitation to their widespread use, especially outside of developed countries.

There is still a major need for the development of additional drugs to circumvent these issues. Ideally these would target different stages in the viral life cycle, adding to the armamentarium for combination therapy, and exhibit minimal toxicity, yet have lower manufacturing costs.

HIV virion assembly takes place at the surface membrane of the infected cell where the viral Gag polyprotein accumulates, leading to the assembly of immature virions that bud from the cell surface. Within the virion, Gag is cleaved by the viral proteinase (PR) into the matrix (MA), capsid (CA), nucleocapsid (NC), and C-terminal p6 structural proteins (Wiegers K. et al., J. Virol. 72:2846-2854 (1998)). Gag processing induces a reorganization of the internal virion structure, a process termed "maturation." In mature HIV particles, MA lines the inner surface of the membrane, while CA forms the conical core which encases the genomic RNA that is complexed with NC. Cleavage and maturation are not required for particle formation but are essential for infectivity (Kohl, N. et al., Proc. Natl. Acad. Sci. USA 85:4686-4690, (1998)).

CA and NC as well as NC and p6 are separated on the Gag polyprotein by short spacer peptides of 14 and 10 amino acids (p2), respectively (spacer peptide 1 (SP1) and SP2, respectively) (Wiegers K. et al., J. Virol. 72:2846-2854 (1998), Pettit, S. C. et al., J. Virol. 68:8017-8027 (1994), Liang et al. J. Virol. 76:11729-11737 (2002)). These spacer peptides are released by PR-mediated cleavages at their N and C termini during particle maturation. The individual cleavage sites on the HIV Gag and Gag-Pol polyproteins are processed at different rates and this sequential processing results in Gag intermediates appearing transiently before the final products. Such intermediates may be important for virion morphogenesis or maturation but do not contribute to the structure of the mature viral particle (Weigers et al. and Pettit, et al., supra). The initial Gag cleavage event occurs at the C terminus of SP1 and separates an N-terminal MA-CA-SP1 intermediate from a C-terminal NC-SP2-p6 intermediate. Subsequent cleavages separating MA from CA-SP1 and NC-SP2 from p6 occur at an approximately 10-fold-lower rate. Cleavage of SP1 from the C terminus of CA is a late event and occurs at a 400-fold-lower rate than cleavage at the SP1-NC site (Weigers et al. and Pettit, et al., supra). The uncleaved CA-SP1 intermediate protein is alternatively termed "p25," whereas the cleaved CA protein is termed "p24."

Cleavage of SP1 from the C terminus of CA appears to be one of the last events in the Gag processing cascade and is required for final capsid condensation and formation of mature, infectious viral particles. Electron micrographs of mature virions reveal particles having electron dense conical cores. On the other hand, electron microscopy studies of viral particles defective for CA-SP1 cleavage show particles having a spherical electron-dense ribonucleoprotein core and a crescent-shaped, electron-dense layer located just inside the viral membrane (Weigers et al., supra). Mutations at or near the CA-SP1 cleavage site have been shown inhibit Gag processing and disrupt the normal maturation process, thereby resulting in the production of non-infectious viral particles (Weigers et al., supra). Phenotypically, these particles exhibit a defect in Gag processing (which manifests itself in the presence of a p25 (CA-SP1) band in Western blot analysis) and the aberrant particle morphology described above which results from defective capsid condensation.

Previously, betulinic acid and platanic acid were isolated from *Syzigium claviflorum* and were determined to have anti-HIV activity. Betulinic acid and platanic acid exhibited inhibitory activity against HIV-1 replication in H9 lymphocyte cells with $EC_{50}$ values of 1.4 μM and 6.5 μM, respectively, and therapeutic index (T.I.) values of 9.3 and 14, respectively. Hydrogenation of betulinic acid yielded dihydrobetulinic acid, which showed slightly more potent anti-HIV activity with an $EC_{50}$ value of 0.9 and a T.I. value of 14 (Fujioka, T., et al., *J. Nat. Prod.* 57:243-247 (1994)). Esterification of betulinic acid with certain substituted acyl groups, such as 3',3'-dimethylglutaryl and 3',3'-dimethylsuccinyl groups produced derivatives having enhanced activity (Kashiwada, Y., et al., *J. Med. Chem.* 39:1016-1017 (1996)). Acylated betulinic acid and dihydrobetulinic acid derivatives that are potent anti-HIV agents are also described in U.S. Pat. No. 5,679,828. Anti-HIV assays indicated that 3-O-(3',3'-dimethylsuccinyl)-betulinic acid and the dihydrobetulinic acid analog both demonstrated extremely potent anti-HIV activity in acutely infected H9 lymphocytes with $EC_{50}$ values of less than $1.7 \times 10^{-5}$ μM, respectively. These compounds exhibited remarkable T.I. values of more than 970,000 and more than 400,000, respectively.

U.S. Pat. No. 5,468,888 discloses 28-amido derivatives of lupanes

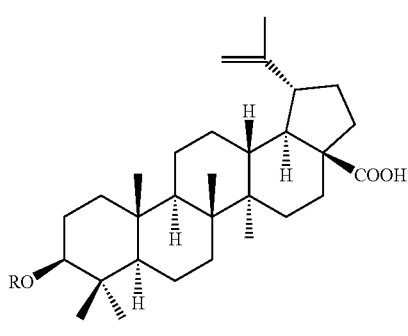

R = H(Betulinic acid)

that are described as having a cytoprotecting effect for HIV-infected cells.

Japanese Patent Application No. JP 01 143,832 discloses that betulin and 3,28-diesters thereof are useful in the anticancer field.

U.S. Pat. No. 6,172,110 discloses betulinic acid and dihydrobetulin derivatives which have the following formulae or pharmaceutically acceptable salts thereof,

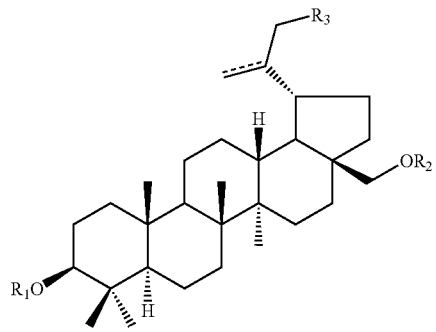

Betulin and Dihydrobetulin Derivatives wherein $R_1$ is a $C_2$-$C_{20}$ substituted or unsubstituted carboxyacyl, $R_2$ is a $C_2$-$C_{20}$ substituted or unsubstituted carboxyacyl; and $R_3$ is hydrogen, halogen, amino, optionally substituted mono- or di-alkylamino, or —$OR_4$, where $R_4$ is hydrogen, $C_{1-4}$ alkanoyl, benzoyl, or $C_2$-$C_{20}$ substituted or unsubstituted carboxyacyl; wherein the dashed line represents an optional double bond between C20 and C29.

U.S. Patent Application No. 60/413,451 discloses 3,3-dimethylsuccinyl betulin and is herein incorporated by reference. Zhu, Y-M. et al., *Bioorg. Chem. Lett.* 11:3115-3118 (2001); Kashiwada Y. et al., *J. Nat. Prod.* 61:1090-1095 (1998); Kashiwada Y. et al., *J. Nat. Prod.* 63:1619-1622 (2000); and Kashiwada Y. et al., *Chem. Pharm. Bull.* 48:1387-1390 (2000) disclose dimethylsuccinyl betulinic acid and dimethylsuccinyl oleanolic acid. Esterification of the 3' carbon of betulin with succinic acid produced a compound capable of inhibiting HIV-1 activity (Pokrovskii, A. G. et al., *Gos. Nauchnyi Tsentr Virusol. Biotekhnol. "Vector,"* 9:485-491 (2001)).

Published International Application No. WO 02/26761 discloses the use of betulin and analogs thereof for treating fungal infections.

There exists a need for new HIV inhibition methods that are effective against drug resistant strains of the virus. The strategy of this invention is to provide therapeutic methods and compounds that inhibit the virus in different ways from approved therapies.

The compound and methods of the present invention have a novel mechanism of action and therefore are active against HIV strains that are resistant to current reverse transcriptase and protease inhibitors. As such, this invention offers a completely new approach for treating HIV/AIDS.

BRIEF SUMMARY OF THE INVENTION

Generally, the invention provides methods of inhibiting, inhibitory compounds and methods of identifying inhibitory compounds that target proteolytic processing of the HIV-1 Gag protein. In one embodiment, such compounds inhibit the interaction of a protease enzyme with HIV-1 Gag protein. In another embodiment, such inhibition of interaction occurs via the binding of a compound to Gag. The inhibition of protease cleavage of the CA-SP1 protein of HIV-1 Gag by 3-O-(3',3'- dimethylsuccinyl) betulinic acid (DSB) is one example, but other proteolytic cleavage sites can be targeted by a similar approach using inhibitory compounds that interact with the substrate in a manner similar to that in which DSB interacts with Gag.

A first aspect of the invention is directed to a method of inhibiting the processing of the viral Gag p25 protein (CA-SP1) to p24 (CA), but having no effect on other Gag processing steps.

A second aspect of the invention is directed to a method for identifying compounds that inhibit processing of the viral Gag p25 protein (CA-SP1) to p24 (CA), but have no effect on other Gag processing steps.

A third aspect of the invention is drawn to a compound or pharmaceutical composition identified by the method for identifying compounds that inhibit HIV-1 replication disclosed herein.

A fourth aspect of the present invention is directed to a polynucleotide comprising a sequence which encodes an amino acid sequence containing a mutation in the Gag p25 protein, said mutation resulting in a decrease in the inhibition of processing of p25 to p24 by 3-O-(3',3'-dimethylsuccinyl) betulinic acid. This aspect of the invention is also directed to a vector, virus and host cell comprising said polynucleotide, and a method of making said protein.

A fifth aspect of the present invention is directed to an amino acid sequence containing a mutation in the Gag p25 protein, said mutation resulting in a decrease in the inhibition of processing of p25 to p24 by 3-O-(3',3'-dimethylsuccinyl) betulinic acid.

A sixth aspect of the invention is directed to an antibody which selectively binds an amino acid sequence containing a mutation in the Gag p25 protein, said mutation resulting in a decrease in the inhibition of processing of p25 to p24 by 3-O-(3',3'-dimethylsuccinyl) betulinic acid. Also included in this aspect of the invention are a method of making said antibody, a hybridoma producing said antibody and a method of making said hybridoma.

A seventh aspect of the invention is directed to a kit comprising a polynucleotide, polypeptide or antibody disclosed herein.

The invention further relates to a method of inhibiting HIV-1 infection in cells of an animal by contacting said cells with a compound that blocks the maturation of virus particles released from treated infected cells. In one embodiment, the released virus particles exhibit non-condensed cores and a distinctive thin electron-dense layer near the viral membrane and have reduced infectivity. A method is included of contacting animal cells with a compound that both inhibits processing of the viral Gag p25 protein and that disrupts the maturation of virus particles. Also, included is a method of treating HIV-infected cells, wherein the HIV infecting said cells does not respond to other HIV therapies.

This invention further includes a method for identifying compounds that inhibit processing of the viral Gag p25 protein (CA-SP1) to p24 (CA), but have no significant effect on other Gag processing steps. The method involves contacting HIV-1 infected cells with a test compound, and thereafter analyzing virus particles that are released to detect the presence of p25. Methods to detect p25 include western blotting of viral proteins and detecting using an antibody to p25, gel electrophoresis, and imaging of metabolically labeled proteins. Methods to detect p25 also include immunoassays using an antibody to p25 or SP1 to distinguish p25 from p24. For example, a microwell assay can be performed where p25 in detergent-solubilized virus is captured using an antibody specific for SP1 that is bound to the plastic microwell plate. Following a washing step, bound p25 is detected using an antibody to p24 that is conjugated to an appropriate detection reagent (e.g. alkaline phosphatase for an enzyme-linked immunosorbent assay). Virus released by cells treated with compounds that act via this mechanism will have increased levels of p25 compared with untreated virions.

The invention is further directed to a method for identifying compounds involving contacting HIV-1 infected cells with a compound, and thereafter analyzing virus particles released by the contacted cells, by thin-sectioning and transmission electron microscopy, and identifying if virion particles are detected with non-condensed cores and a distinctive thin electron-dense layer near the viral membrane.

The invention is also directed to compounds identified by the aforementioned screening methods.

BRIEF DESCRIPTION OF THE DRAWINGS/FIGURES

FIG. 1. DSB does not disrupt the activity of HIV-1 protease at a concentration of 50 µg/mL. In DSB-containing samples recombinant Gag is processed correctly. In contrast, indinavir blocks protease activity at 5 µg/mL as evidenced by the absence of bands corresponding to p24 and the MA-CA precursor.

FIG. 2. Western blots of virion-associated Gag derived from chronically infected H9/HIV-1$_{IIIB}$, H9/HIV-2$_{ROD}$, and H9/SIV$_{mac251}$ in the presence of DSB (1 µg/mL), indinavir (1 µg/mL) or control (DMSO). Gag proteins were visualized using HIV-Ig (HIV-1) or monkey anti-SIV$_{mac251}$ serum (HIV-2 and SIV; NIH AIDS Research and Reference Reagent Program).

FIG. 3. EM analysis of DSB-treated HIV-1 infected cells. The EM data show two primary differences between DSB-treated and untreated samples. Virions generated in the presence of DSB are characterized by an absence of conical, mature cores. In these samples the cores are uniformly spherical and often acentric. Secondly, many virions display an electron dense layer inside the lipid bilayer but outside the core (indicated with arrows in the DSB-treated sample panels). In the DSB-treated samples no mature viral particles were observed.

FIG. 4 depicts a amino acid sequences in the region of the CA-SP1 cleavage site from DSB-sensitive HIV-1 isolates NL4-3 and RF (#1; SEQ ID NO: 1) and DSB-resistant HIV-1 isolates (#2; SEQ ID NO: 2 (NL4-3), and #3; SEQ ID NO: 12 (RF)). The differences between the native and DSB-resistant sequences involve an alanine to valine change at the first downstream residue (#2) and an alanine to valine change in the third downstream residue (#3) from the CA-SP1 cleavage site (-|-). These residues are underlined and bolded for ease of identification.

FIG. 5 depicts the + sense consensus sequence for the A364V DSB-resistant NL4-3 mutant (SEQ ID NO: 4) beginning with the start of the gag coding sequence and continuing into pol, including the entire protease coding region. Missense mutations not found in the wild-type NL4-3 GENBANK M19921 sequence are in bold and gray shadowing. The coding sequence for the consensus CA-SP1 cleavage site is underlined. The shaded area including the cleavage site denotes the SP1 sequence. The first mutation is the A364V mutation; the second amino acid difference (in protease) was also found in the parental clone and has been confirmed to correspond to a sequencing error in the original GENBANK entry. Therefore, no mutations actually occurred in protease.

FIG. 6 depicts the + sense consensus sequence for the DSB-sensitive NL4-3 parental isolate (SEQ ID NO: 5) that was passaged in the absence of drug in parallel with the A364V mutant isolate.

FIG. 7 depicts the + sense consensus sequence for the A366V DSB-resistant HIV-1$_{RF}$ mutant (SEQ ID NO: 6) beginning with the start of the Gag coding sequence and continuing through all of the coding sequence for Pro and part of RT. Missense mutations not found in the wild-type HIV-1$_{RF}$ GENBANK M17451 sequence are shadowed in gray. The CA-SP1 cleavage site is underlined. The only missense mutation not also found in the identically passaged DSB-sensitive isolate is the A366V mutation in the CA-SP1 cleavage site.

FIG. 8 depicts the + sense consensus sequence for the DSB-sensitive HIV-1$_{RF}$ parental isolate (SEQ ID NO: 7), that was passaged in the absence of drug in parallel with the A366V mutant isolate.

FIG. 9 depicts the polynucleotide sequences, SEQ ID NO: 8 and SEQ ID NO: 9, which encode the polypeptides designated herein as SEQ ID NO: 2 and SEQ ID NO: 3, respectively. SEQ ID NO: 10 depicts the nucleotide sequence that encodes the parental polypeptide sequence designated herein as SEQ ID NO: 1.

FIG. 10 depicts the amino acid sequence from SIV$_{mac239}$ in the region of the CA-SP1 cleavage site (-|-) (SEQ ID NO: 11).

DETAILED DESCRIPTION OF THE INVENTION

Figure 1:
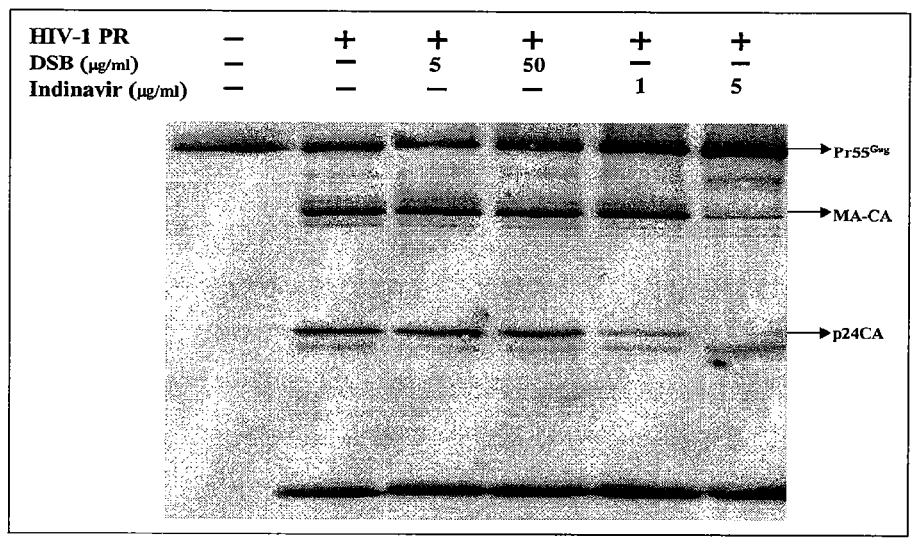

The present invention is directed to methods of inhibiting HIV-1 replication in the cells of an animal that involve using compounds that disrupt the processing of the viral Gag p25 protein (CA-SP1) to the p24 protein (CA), thereby resulting in the formation of non-infectious viral particles.

Mutant viruses defective in CA-SP1 cleavage have been shown to be non-infectious (Wiegers K. et al., *J. Virol.* 72:2846-2854 (1998)). 3-O-(3',3'-dimethylsuccinyl) betulinic acid (DSB) is an example of a compound that disrupts p25 to p24 processing and potently inhibits HIV-1 replication. This compound's activity is specific for the p25 to p24 processing step, not other steps in Gag processing. Furthermore, DSB treatment results in the aberrant HIV particle morphology as described in FIG. 3.

Mutant forms of HIV-1 have been generated in which the SP1 sequence is modified making these strains resistant to compounds that disrupt CA-SP1 processing. Data on these mutant viruses have been used to identify the amino acid residues in native Gag that are implicated in the antiviral activity of these compounds. In one embodiment, compounds that disrupt CA-SP1 processing inhibit the interaction of HIV-1 protease with the region of the Gag protein containing these amino acid residues. In another embodiment, compounds that disrupt CA-SP1 processing bind to the region containing these amino acid residues. In another embodiment, compounds that disrupt CA-SP1 processing bind to another region of Gag and thereby inhibit the interaction of HIV-1 protease with the region of the CA-SP1 cleavage site. In another embodiment, viruses or recombinant proteins that contain mutations in the region of the CA-SP1 cleavage site can be used in screening assays to identify compounds that disrupt CA-SP1 processing.

Amino acid residues in HIV-1 Gag that are involved in the disruption of CA-SP1 processing by 3-O-(3',3'-dimethylsuccinyl) betulinic acid (DSB) were identified by sequencing the Gag-Pol gene of virus isolates that had been selected for resistance to DSB. The amino acid sequences from these resistant viruses were compared with the Gag-Pol gene sequences from DSB-sensitive HIV-1 isolates. Two single amino acid changes were identified in the DSB-resistant viruses, an alanine (Ala) to valine (Val) substitution at residue 364 (SEQ ID NO: 4) and in a second isolate, at residue 366 (SEQ ID NO: 6), in the Gag polyprotein (see FIG. 4). These residues are located immediately downstream of the CA-SP1 cleavage site (at the N-terminus of SP 1). Alanine is highly conserved at these positions throughout all HIV-1 clades in the Los Alamos National Laboratory database. The five amino acid residues upstream and downstream of the CA-SP1 cleavage site are also highly conserved among the various clades. However, isoleucine replaces vailine at the position two residues upstream of the cleavage site in a number of clades (c.f., FIG. 4, SEQ ID NO: 1). ("*HIV Sequence Compendium 2002*," Kuiken et al. eds. Los Alamos National Laboratory, Los Alamos, N. Mex.)

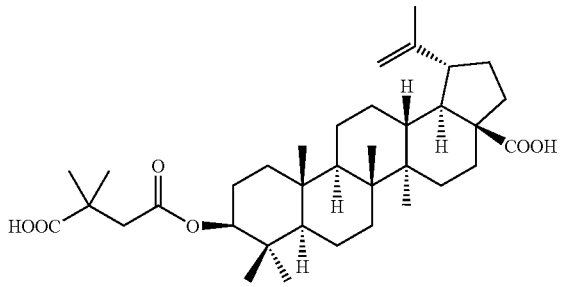

Structure of 3-O-(3',3'-dimethylsuccinyl) betulinic acid (DSB)

The invention also includes a method of inhibiting HIV-1 replication in cells of an animal comprising contacting infected cells with a compound that inhibits the interaction of HIV protease with CA-SP1 which results in the inhibition of the processing of the viral Gag p25 protein (CA-SP1) to p24 (CA), but has no significant effect on other Gag processing steps.

The invention is also drawn to a method of inhibiting HIV-1 replication in cells of an animal comprising contacting infected cells with a compound that inhibits processing of the viral Gag p25 protein (CA-SP1) to p24 (CA), thereby causing the viral particles that are released to be non-infectious, but has no significant effect on other Gag processing steps and/or wherein said inhibition does not significantly reduce the quantity of virus released from treated cells and/or has no significant effect on the amount of RNA incorporation into the released virions. The invention is also drawn to a method of inhibiting HIV-1 replication in cells of an animal comprising contacting infected cells with a compound that inhibits the maturation of virus particles released from treated infected cells. In one embodiment, these released viral particles exhibit spherical, electron-dense cores that are acentric with respect to the viral particles, rather than the conical core structures associated with mature viral particles and possess crescent-shaped, electron-dense layers lying just inside the viral membrane and have reduced or no infectivity. Some viral particles may also exhibit a conical core structure along with a preponderance of the viral particles that exhibit the altered core structure described above.

Abnormal p25 to p24 processing is also seen in other maturation budding defects (Wild, C. T. et al., *XIV Int. AIDS Conf.*, Barcelona, Spain, Abstract MoPeA3030 (July 2002)). These defects included mutations in the Gag late domain (PTAP) or defects in TSG-101 mediated viral assembly that disrupt budding (Garrus, J. E et al., *Cell,* 107:55-65 (2001)

and Demirov, D. G. et al., *J. Virology* 76:105-117 (2002)). However, these mutations cause inhibition of virus release, while DSB treatment does not have a significant effect on virus release. The morphology of these maturation/budding mutants is also quite distinct from that observed following DSB-treatment. In addition, mutations that interfere with viral RNA dimerization and lead to the production of immature virus with defective core structures give a similar Gag processing phenotype (Liang, C. et al., *J. Virology*, 73:6147-6151, (1999)). However, in those cases RNA incorporation is inhibited and the morphology of particles released is distinct from those following DSB treatment.

The method of inhibiting an HIV-1 replication in cells of an animal disclosed herein includes a compound which binds near to or at the site of cleavage of the viral Gag p25 protein (CA-SP1) to p24 (CA), thereby inhibiting the interaction of HIV protease with the CA-SP1 cleavage site.

The invention includes any of the disclosed methods, wherein the HIV infecting said cells does not respond to other HIV therapies.

The present invention comprises a polynucleotide comprising a sequence which encodes an amino acid sequence containing a mutation in the HIV Gag p25 protein (CA-SP1), said mutation resulting in a decrease in the inhibition of processing of p25 (CA-SP1) to p24 (CA) by DSB. The polynucleotide of the invention includes a mutation which is optionally located near the CA-SP1 cleavage site or located in the SP1 region of CA-SP1. Said mutation can be present in an amino acid sequence that is selected from the group consisting of KARVLVEAMS (SEQ ID NO: 2) or KARILAEVMS (SEQ ID NO: 3). The polynucleotide of this invention is also drawn to sequences designated as SEQ ID NO: 4, SEQ ID NO: 6, SEQ ID NO: 8 or SEQ ID NO: 9. The invention also includes a vector comprising said polynucleotide, a host cell comprising said vector and a method of producing said polypeptides comprising incubating said host cell in a medium and recovering the polypeptide from the medium.

The invention further includes a polynucleotide that hybridizes under stringent conditions to a polynucleotide selected from the group consisting of SEQ ID NO: 4, SEQ ID NO: 6, SEQ ID NO: 8 or SEQ ID NO: 9. The invention also includes a polynucleotide which hybridizes to SEQ NO: 5, SEQ ID NO: 7 or SEQ ID NO: 10, which contains a mutation which results in the decrease in the inhibition of processing of p25 to p24 by 3-O-(3',3'-dimethylsuccinyl) betulinic acid, and also wherein said mutation is optionally located in the SP1 region of CA-SP1. The invention is also directed to a vector comprising said polynucleotides, a host cell comprising said vector and a method of producing said polypeptides, comprising incubating said host cell in a medium and recovering said polypeptide from the medium.

"Isolated" means altered "by the hand of man" from the natural state. If an "isolated" composition or substance occurs in nature, it has been changed or removed from its original environment, or both. Also, "isolated" nucleic acid molecule(s) of the invention is intended a nucleic acid molecule, DNA or RNA, which has been removed from its native environment. For example, recombinant DNA molecules contained in a vector are considered isolated for the purposes of the present invention. Further examples of isolated DNA molecules include recombinant DNA molecules maintained in heterologous host cells or purified (partially or substantially) DNA molecules in solution. Isolated RNA molecules include in vivo or in vitro RNA transcripts of the DNA molecules of the present invention. Isolated nucleic acid molecules according to the present invention further include such molecules produced synthetically.

"Polynucleotide" generally refers to any polyribonucleotide or polydeoxyribonucleotide, which may be unmodified RNA or DNA or modified RNA or DNA. "Polynucleotides" include, without limitation single- and double-stranded DNA, DNA that is a mixture of single- and double-stranded regions, single- and double-stranded RNA, and RNA that is mixture of single- and double-stranded regions, hybrid molecules comprising DNA and RNA that may be single-stranded or, more typically, double-stranded or a mixture of single- and double-stranded regions. In addition, "polynucleotide" refers to triple-stranded regions comprising RNA or DNA or both RNA and DNA. The term polynucleotide also includes DNAs or RNAs containing one or more modified bases and DNAs or RNAs with backbones modified for stability or for other reasons. "Modified" bases include, for example, tritiated bases and unusual bases such as inosine. A variety of modifications has been made to DNA and RNA; thus, "polynucleotide" embraces chemically, enzymatically or metabolically modified forms of polynucleotides as typically found in nature, as well as the chemical forms of DNA and RNA characteristic of viruses and cells. "Polynucleotide" also embraces relatively short polynucleotides, often referred to as oligonucleotides.

"Polypeptide" refers to any peptide or protein comprising two or more amino acids joined to each other by peptide bonds or modified peptide bonds, i.e., peptide isosteres. "Polypeptide" refers to both short chains, commonly referred to as peptides, oligopeptides or oligomers, and to longer chains, generally referred to as proteins. Polypeptides may contain amino acids other than the 20 gene-encoded amino acids. "Polypeptides" include amino acid sequences modified either by natural processes, such as post-translational processing, or by chemical modification techniques which are well known in the art. Such modifications are well described in basic texts and in more detailed monographs, as well as in a voluminous research literature. Modifications can occur anywhere in a polypeptide, including the peptide backbone, the amino acid side-chains and the amino or carboxyl termini. It will be appreciated that the same type of modification may be present in the same or varying degrees at several sites in a given polypeptide. Also, a given polypeptide may contain many types of modifications. Polypeptides may be branched as a result of ubiquitination, and they may be cyclic, with or without branching. Cyclic, branched and branched cyclic polypeptides may result from posttranslation natural processes or may be made by synthetic methods. Modifications include acetylation, acylation, ADP-ribosylation, amidation, covalent attachment of flavin, covalent attachment of a heme moiety, covalent attachment of a nucleotide or nucleotide derivative, covalent attachment of a lipid or lipid derivative, covalent attachment of phosphotidylinositol, cross-linking, cyclization, disulfide bond formation, demethylation, formation of covalent cross-links, formation of cystine, formation of pyroglutamate, formylation, gamma-carboxylation, glycosylation, GPI anchor formation, hydroxylation, iodination, methylation, myristoylation, oxidation, proteolytic processing, phosphorylation, prenylation, racemization, selenoylation, sulfation, transfer-RNA mediated addition of amino acids to proteins such as arginylation, and ubiquitination.

"Mutant" as the term is used herein, is a polynucleotide or polypeptide that differs from a reference polynucleotide or polypeptide respectively, but retains essential properties. A typical mutant of a polynucleotide differs in nucleotide sequence from another, reference polynucleotide. Changes in the nucleotide sequence of the mutant may or may not alter the amino acid sequence of a polypeptide encoded by the reference polynucleotide. Nucleotide changes may result in amino acid substitutions, additions, deletions, fusions and truncations in the polypeptide encoded by the reference sequence, as discussed below. A typical mutant of a polypeptide differs in amino acid sequence from another, reference polypeptide. Generally, differences are limited so that the sequences of the reference polypeptide and the variant are closely similar overall and, in many regions, identical. A mutant and reference polypeptide may differ in amino acid sequence by one or more substitutions, additions, deletions in any combination. A substituted or inserted amino acid residue may or may not be one encoded by the genetic code. A mutant of a polynucleotide or polypeptide may be a naturally occurring such as an allelic variant, or it may be a mutant that is not known to occur naturally. Non-naturally occurring mutants of polynucleotides and polypeptides may be made by mutagenesis techniques or by direct synthesis.

Thus, the mutant, (or fragments, derivatives or analogs) of a polypeptide encoded by any one of the polynucleotides described herein may be (i) one in which at least one or more of the amino acid residues are substituted with a conserved or non-conserved amino acid residue (a conserved amino acid residue(s), or at least one but less than ten conserved amino acid residues) and such substituted amino acid residue may or may not be one encoded by the genetic code, (ii) one in which one or more of the amino acid residues includes a substituent group, (iii) one in which the mature polypeptide is fused with another compound, such as a compound to increase the half-life of the polypeptide (for example, polyethylene glycol), or (iv) one in which the additional amino acids are fused to the mature polypeptide, such as an IgG:Fc fusion region peptide or leader or secretory sequence or a sequence which is employed for purification of the mature polypeptide or a proprotein sequence. Such mutants are deemed to be within the scope of those skilled in the art from the teachings herein. Polynucleotides encoding these mutants are also encompassed by the invention. "Mutant" as used herein is equivalent to the term "variant."

Substitutions of charged amino acids with another charged amino acids and with neutral or negatively charged amino acids are included. Additionally, one or more of the amino acid residues of the polypeptides of the invention (e.g., arginine and lysine residues) may be deleted or substituted with another residue to eliminate undesired processing by proteases such as, for example, furins or kexins. The prevention of aggregation is highly desirable. Aggregation of proteins not only results in a loss of activity but can also be problematic when preparing pharmaceutical formulations, because they can be immunogenic. (Pinckard et al., *Clin Exp. Immunol.* 2:331-340 (1967); Robbins et al., Diabetes 36:838-845 (1987); Cleland et al. *Crit. Rev. Therapeutic Drug Carrier Systems* 10:307-377 (1993)). Thus, the polypeptides of the present invention may include one or more amino acid substitutions, deletions or additions, either from natural mutations or human manipulation.

As indicated, changes are preferably of a minor nature, such as conservative amino acid substitutions that do not significantly affect the folding or activity of the protein (see Table 1).

TABLE 1

Conservative Amino Acid Substitutions

| | |
|---|---|
| Aromatic | Phenylalanine |
| | Tryptophan |
| | Tyrosine |

TABLE 1-continued

Conservative Amino Acid Substitutions

| | |
|---|---|
| Hydrophobic | Leucine |
| | Isoleucine |
| | Valine |
| Polar | Glutamine |
| | Asparagine |
| Basic | Arginine |
| | Lysine |
| | Histidine |
| Acidic | Aspartic Acid |
| | Glutamic Acid |
| Small | Alanine |
| | Serine |
| | Threonine |
| | Methionine |
| | Glycine |

The polynucleotides encompassed by this invention may have 45%, 50%, 55%, 60%, 65%, 70%, 75%, 80%, 85%, 90%, or 95% identity with a reference sequence, providing the reference polynucleotide encodes an amino acid sequence containing a mutation in the CA-SP1 protein, said mutation which results in the decrease in the inhibition of processing of p25 to p24 by a 3-O-(3',3'-dimethylsuccinyl) betulinic acid. The polynucleotides also encompassed by this invention include those mutations which are "silent," in which different codons encode the same amino acid (wobble).

“Identity” is a measure of the identity of nucleotide sequences or amino acid sequences. The term “identity” is used interchangeably with the word “homology” herein. In general, the sequences are aligned so that the highest order match is obtained. “Identity” per se has an art-recognized meaning and can be calculated using published techniques. While there exist a number of methods to measure identity between two polynucleotide or polypeptide sequences, the term “identity” is well known to skilled artisans. Methods commonly employed to determine identity or similarity between two sequences include, but are not limited to, those disclosed in Baxevanis and Oullette, *Bioinformatics: A Practical Guide to the Analysis of Genes and Proteins, Second Edition*, Wiley-Interscience, New York, (2001). Methods to determine identity and similarity are codified in computer programs. Preferred computer program methods to determine identity and similarity between two sequences include, but are not limited to, GCS program package (Devereux, J. et al., *Nucleic Acids Research* 12(1):387, (1984)), BLASTP, BLASTN, FASTA (Atschul, S. F. et al., *J. Molec. Biol.* 215: 403, (1990)).

A polynucleotide having a nucleotide sequence having at least, for example, 95% “identity” to a reference nucleotide sequence is intended that the nucleotide sequence of the polynucleotide is identical to the reference sequence except that the polynucleotide sequence may include up to five point mutations per each 100 nucleotides of the reference nucleotide sequence, up to 5% of the nucleotides in the reference sequence may be deleted or substituted with another nucleotide, or a number of nucleotides up to 5% of the total nucleotides in the reference sequence may be inserted into the reference sequence. These mutations of the reference sequence may occur at the 5' or 3' terminal positions of the reference nucleotide sequence or anywhere between those terminal positions, interspersed either individually among nucleotides in the reference sequence or in one or more contiguous groups within the reference sequence.

Similarly, by a polypeptide having an amino acid sequence having at least, for example, 95% “identity” to a reference amino acid sequence, is intended that the amino acid sequence of the polypeptide is identical to the reference sequence except that the polypeptide sequence may include up to five amino acid alterations per each 100 amino acids of the reference amino acid. To obtain a polypeptide having an amino acid sequence at least 95% identical to a reference amino acid sequence, up to 5% of the amino acid residues in the reference sequence may be deleted or substituted with another amino acid, or a number of amino acids up to 5% of the total amino acid residues in the reference sequence may be inserted into the reference sequence. These alterations of the reference sequence may occur at the amino or carboxy terminal positions of the reference amino acid sequence or anywhere between those terminal positions, interspersed either individually among residues in the reference sequence or in one or more contiguous groups within the reference sequence. The reference (query) sequence may be the entire nucleotide sequence of any one of the nucleotide sequences of the invention or any polynucleotide fragment (e.g., a polynucleotide encoding the amino acid sequence of the invention and/or C terminal deletion).

Whether any particular nucleic acid molecule is at least 80%, 85%, 90%, 92%, 95%, 96%, 97%, 98% or 99% identical to, for instance, the nucleotide sequences of the invention can be determined conventionally using known computer programs such as the BESTFIT program (Wisconsin Sequence Analysis Package, Version 8 for Unix, Genetics Computer Group, University Research Park, 575 Science Drive, Madison, Wis. 53711). BESTFIT uses the local homology algorithm of Smith and Waterman, (*Advances in Applied Mathematics* 2:482-489 (1981)), to find the best segment of homology between two sequences. When using BESTFIT or any other sequence alignment program to determine whether a particular sequence is, for instance, 95% identical to a reference sequence according to the present invention, the parameters are set, such that the percentage of identity is calculated over the full length of the reference nucleotide sequence and that gaps in homology of up to 5% of the total number of nucleotides in the reference sequence are allowed.

In a specific embodiment, the identity between a sequence of the present invention and a subject sequence, also referred to as a global sequence alignment, is determined using the FASTDB computer program based on the algorithm of Brutlag et al. (*Comp. App. Biosci.* 6:237-245 (1990)). Preferred parameters used in a FASTDB alignment of DNA sequences to calculate percent identity are: Matrix=Unitary, k-tuple=4, Mismatch Penalty=1, Joining Penalty=30, Randomization Group Length=0, Cutoff Score=1, Gap Penalty=5, Gap Size Penalty 0.05, Window Size=500 or the length of the subject nucleotide sequence, whichever is shorter. According to this embodiment, if the subject sequence is shorter than the reference sequence because of 5' or 3' deletions, not because of internal deletions, a manual correction is made to the results to take into consideration the fact that the FASTDB program does not account for 5' and 3' truncations of the subject sequence when calculating percent identity. For subject sequences truncated at the 5' or 3' ends, relative to the query sequence, the percent identity is corrected by calculating the number of bases of the query sequence that are 5' and 3' of the subject sequence, which are not matched/aligned, as a percent of the total bases of the query sequence. A determination of whether a nucleotide is matched/aligned is determined by results of the FASTDB sequence alignment. This percentage is then subtracted from the percent identity, calculated by the above FASTDB program using the specified parameters, to arrive at a final percent identity score. This corrected score is what is used for the purposes of this embodiment. Only bases outside the 5' and 3' bases of the subject sequence, as displayed by the FASTDB alignment, which are not matched/aligned with the query sequence, are calculated for the purposes of manually adjusting the percent identity score. For example, a 90 base subject sequence is aligned to a 100 base query sequence to determine percent identity. The deletions occur at the 5' end of the subject sequence and therefore, the FASTDB alignment does not show a matched/alignment of the first 10 bases at 5' end. The 10 unpaired bases represent 10% of the sequence (number of bases at the 5' and 3' ends not matched/total number of bases in the query sequence) so 10% is subtracted from the percent identity score calculated by the FASTDB program. If the remaining 90 bases were perfectly matched the final percent identity would be 90%. In another example, a 90 base subject sequence is compared with a 100 base query sequence. This time the deletions are internal deletions so that there are no bases on the 5' or 3' of the subject sequence, which are not matched/aligned with the query. In this case the percent identity calculated by FASTDB is not manually corrected. Only bases 5' and 3' of the subject sequence which are not matched/aligned with the query sequence are manually corrected. No other manual corrections are made for the purposes of this embodiment.

The present application is directed to nucleic acid molecules at least 80%, 85%, 90%, 92%, 95%, 96%, 97%, 98% or 99% identical to the nucleic acid sequence disclosed herein, or fragments thereof, irrespective of whether they encode a polypeptide having the disclosed functional activity. This is because even where a particular nucleic acid molecule does not encode a polypeptide having the disclosed functional activity, one of skill in the art would still know how to use the nucleic acid molecule, for instance, as a hybridization probe or a polymerase chain reaction (PCR) primer. Uses of the nucleic acid molecules of the present invention that do not encode a polypeptide having the disclosed functional activity include, inter alia: (1) isolating the variants thereof in a cDNA library; (2) in situ hybridization (e.g., "FISH") to determine cellular location or presence of the disclosed sequences, and (3) Northern Blot analysis for detecting mRNA expression in specific tissues.

As used herein, the term "PCR" refers to the polymerase chain reaction that is the subject of U.S. Pat. Nos. 4,683,195 and 4,683,202 to Mullis et al., as well as improvements now known in the art. In accordance with the present invention there may be employed conventional molecular biology, microbiology, and recombinant DNA techniques within the skill of the art. Such techniques are explained fully in the literature. See, for example, Sambrook, J. and Russell, D. W. (2001) *Molecular Cloning: A Laboratory Manual,* 3rd Ed., Cold Spring Harbor Laboratory Press, Cold Spring Harbor, N.Y.

The term "stringent conditions," as used herein refers to homology in hybridization, is based upon combined conditions of salt, temperature, organic solvents, and other parameters typically controlled in hybridization reactions, and well known in the art (Sambrook, et al. supra). The invention includes an isolated nucleic acid molecule comprising, a polynucleotide which hybridizes under stringent hybridization conditions to a portion of the polynucleotide in a nucleic acid molecule of the invention described above, for instance, the sequence complementary to the coding and/or noncoding (i.e., transcribed, untranslated) sequence of any polynucleotide or a polynucleotide fragment as described herein. By "stringent hybridization conditions" is intended overnight incubation at 42° C. in a solution comprising, or alternatively consisting of: 50% formamide, 5×SSC (750 mM NaCl, 75 mM trisodium citrate), 50 mM sodium phosphate (pH 7.6), 5×Denhardt's solution, 10% dextran sulfate, and 20 µg/ml denatured, sheared salmon sperm DNA, followed by washing in 0.1×SSC at about 65° C. Polypeptides encoded by these polynucleotides are also encompassed by the invention.

"Near" or "adjacent," as used herein is meant to include about 15 residues on either side of the HIV-1 Gag CA-SP1 cleavage site; more preferably about 10 residues on either side of the HIV-1 Gag CA-SP1 cleavage site; and most preferably about 5 residues on either side of the HIV-1 Gag CA-SP1 cleavage site.

"Significantly," where not otherwise defined herein, means +/− that observed or measured compared to the process or processing that would occur in the absence of the compound.

The invention also includes a virus comprising the polynucleotides of the invention, and wherein the virus includes a retrovirus comprising said polynucleotides, and wherein the retrovirus may be a member of the group consisting of HIV-1, HIV-2, HTLV-I, HTLV-II, SW, avian leukosis virus (ALV), endogenous avian retrovirus (EAV), mouse mammary tumor virus (MMTV), feline immunodeficiency virus (FIV), or feline leukemia virus (FeLV).

The invention further includes a polypeptide containing a mutation in the CA-SP1 protein, said mutation which results in the decrease in inhibition of processing of p25 to p24 by 3-O-(3',3'-dimethylsuccinyl) betulinic acid, and also wherein said mutation is optionally located near the CA-SP1 cleavage site or located in the SP1 region of SEQ ID NO: 5 or SEQ ID NO: 7 (parental polynucleotide sequences) encoding the CA-SP1 protein. Said polypeptide may be encoded by a polynucleotide selected from the group consisting of SEQ ID NO: 4, SEQ ID NO: 6, SEQ ID NO: 8 or SEQ ID NO: 9, or may comprise a sequence that is selected from the group consisting of KARVLVEAMS (SEQ ID NO: 2) or KARILAEVMS (SEQ ID NO: 3). The polypeptide of this invention may further be encoded by a polynucleotide which hybridizes under highly stringent conditions to a polynucleotide selected from the group consisting of SEQ ID NO: 4, SEQ ID NO: 6, SEQ ID NO: 8 or SEQ ID NO: 9. The invention also includes a polypeptide encoded by a polynucleotide which hybridizes to SEQ NO: 5, SEQ ID NO: 7 or SEQ ID NO: 10, which contains a mutation that results in decrease in inhibition of processing of p25 to p24 by 3-O-(3',3'-dimethylsuccinyl) betulinic acid, and also wherein said mutation is optionally located in the SP1 region of CA-SP1. The polypeptide of this invention further includes polypeptides that are part of a chimeric or fusion protein. Said chimeric proteins may be derived from species which include, but are not limited to: primates, including simian and human; rodentia, including rat and mouse; feline; bovine; ovine; including goat and sheep; canine; or porcine. Fusion proteins may include synthetic peptide sequences, bifunctional antibodies, peptides linked with proteins from the above species, or with linker peptides. Polypeptides of the invention may be further linked with detectable labels; metal compounds; cofactors; chromatography separation tags, such as, but not limited to: histidine, protein A, or the like, or linkers; blood stabilization moieties such as, but not limited to: transferrin, or the like; therapeutic agents, and so forth.

The invention also includes an antibody which selectively binds an amino acid sequence containing a mutation in the CA-SP1 protein that results in a decrease in the inhibition of processing of p25 (CA-SP1) to p24 (CA) by 3-O-(3',3'-dimethylsuccinyl) betulinic acid and also wherein said mutation is optionally located in the SP1 region of CA-SP1. The invention also includes an antibody which selectively binds the polypeptide having a mutation which comprises a sequence that is one of KARVLVEAMS (SEQ ID NO: 2), KARILAE-VMS (SEQ ID NO: 3). Said antibody can selectively bind the polypeptide encoded by a polynucleotide sequence selected from the group consisting of SEQ ID NO: 4, SEQ ID NO: 6, SEQ ID NO: 8 or SEQ ID NO: 9. Said antibody can also selectively bind the polypeptide encoded by a polynucleotide which hybridizes under highly stringent conditions to a polynucleotide selected from the group consisting of SEQ ID NO: 4, SEQ ID NO: 6, SEQ ID NO: 8 and SEQ ID NO: 9. The invention also includes an antibody that is selectively binds to SP1, which would enable one to distinguish SP1 from CA-SP1. The invention also includes an antibody that selectively binds CA, which would enable one to distinguish CA from CA-SP1. The invention additionally includes an antibody that selectively binds at or near the CA-SP1 cleavage site. The antibody of this invention may be a polyclonal antibody, a monoclonal antibody or said antibody may be chimeric or bifunctional, or part of a fusion protein. The invention further includes a portion of any antibody of this invention, including single chain, light chain, heavy chain, CDR, F(ab')$_2$, Fab, Fab', Fv, sFv, or dsFv, or any combinations thereof.

As used herein, an antibody "selectively binds" a target peptide when it binds the target peptide and does not significantly bind to unrelated proteins. The term "selectively binds" also comprises determining whether the antibody selectively binds to the target mutant sequence relative to a native target sequence. An antibody which "selectively binds" a target peptide is equivalent to an antibody which is "specific" to a target peptide, as used herein. An antibody is still considered to selectively bind a peptide even if it also binds to other proteins that are not substantially homologous with the target peptide so long as such proteins share homology with a fragment or domain of the peptide target of the antibody. In this case, it would be understood that antibody binding to the peptide is still selective despite some degree of cross-reactivity. In another embodiment, the determination whether the antibody selectively binds to the mutant target sequence comprises: (a) determining the binding affinity of the antibody for the mutant target sequence and for the native target sequences; and (b) comparing the binding affinities so determined, the presence of a higher binding affinity for the mutant target sequence than for the native indicating that the antibody selectively binds to the mutant target sequence.

The invention is further drawn to an antibody immobilized on an insoluble carrier comprising any of the antibodies disclosed herein. The antibody immobilized on an insoluble carrier includes multiple well plates, culture plates, culture tubes, test tubes, beads, spheres, filters, electrophoresis material, microscope slides, membranes, or affinity chromatography medium.

The invention also includes labeled antibodies, comprising a detectable signal. The labeled antibodies of this invention are labeled with a detectable molecule, which includes an enzyme, a fluorescent substance, a chemiluminescent substance, horseradish peroxidase, alkaline phosphatase, biotin, avidin, an electron dense substance, and a radioisotope, or any combination thereof.

The invention further includes a method of producing a hybridoma comprising fusing a mammalian myeloma cell with a mammalian B cell that produces a monoclonal antibody which selectively binds an amino acid sequence containing a mutation in the CA-SP1 protein, said mutation resulting in a decrease in the inhibition of processing of p25 to p24 by 3-O-(3',3'-dimethylsuccinyl) betulinic acid and a hybridoma producing any of the monoclonal antibodies disclosed herein. The invention further includes a method of producing an antibody comprising growing a hybridoma producing the monoclonal antibodies disclosed herein in an appropriate medium and isolating the antibodies from the medium, as is well known in the art. The invention also includes the production of polyclonal antibodies comprising the injection, either one injection or multiple injections of any of the polypeptides of the inventions into any animal known in the art to be useful for the production of polyclonal antibodies, including, but not limited to mouse, rat, hamster, rabbit, goat, sheep, deer, guinea pig, or primate, and recovering the antibodies in sera produced therein. The invention includes high avidity or high affinity antibodies produced therein. The invention also includes B cells produced from the listed species to be further used in cell fusion procedures for the manufacture of monoclonal antibody-producing hybridomas as disclosed herein.

The invention is further drawn to a kit comprising the antibody or a portion thereof as disclosed herein, a container comprising said antibody and instructions for use, a kit comprising the polypeptides of this invention and instructions for use and a kit comprising the polynucleotide of the invention, a container comprising said polynucleotide and instructions for use, or any combinations thereof. These kits would include, but not be limited to nucleic acid detection kits, which may, or may not, utilize PCR and immunoassay kits. Such kits are useful for clinical diagnostic use and provide standardized reagents as required in current clinical practice. These kits could either provide information as to the presence or absence of mutations prior to treatment or monitor the progress of the patient during therapy. The kits of the invention may also be used to provide standardized reagents for use in research laboratory studies.

Compounds useful in the present invention include, but are not limited to those having the general Formula I and II:

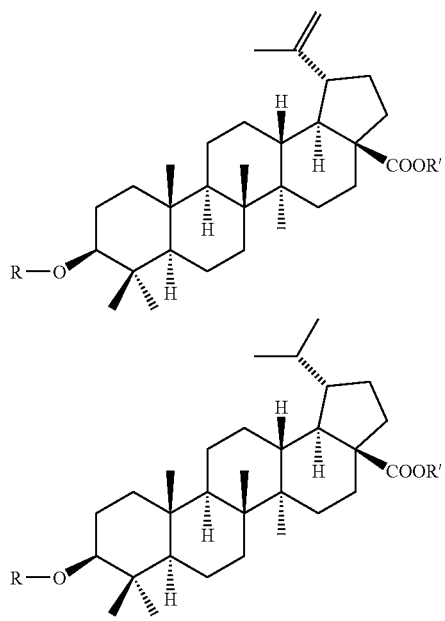

I: Derivatives of Betulinic Acid (left) and Dihydrobetulinic Acid (right),
or a pharmaceutically acceptable salt thereof, wherein,
R is a $C_2$-$C_{20}$ substituted or unsubstituted carboxyacyl,
R' is hydrogen or a $C_2$-$C_{10}$ substituted and unsubstituted alkyl or aryl group. Preferred compounds are those wherein R is one of the substituents in Table 2 and R' is hydrogen.

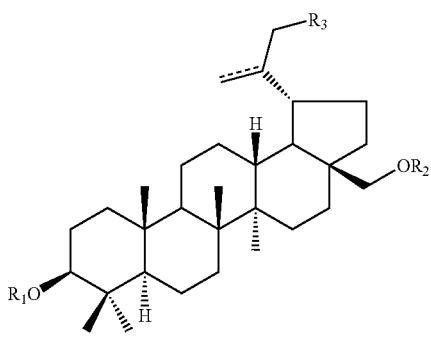

II: Derivatives of betulin and dihydrobetulin,
or a pharmaceutically acceptable salt thereof, wherein,
R$_1$ is a $C_2$-$C_{20}$ substituted or unsubstituted carboxyacyl,
R$_2$ is hydrogen or a $C_2$-$C_{20}$ substituted or unsubstituted carboxyacyl; and
R$_3$ is hydrogen, halogen, amino, optionally substituted mono- or di-alkylamino, or —OR$_4$, where R$_4$ is hydrogen, $C_{1-4}$ alkanoyl, benzoyl, or $C_2$-$C_{20}$ substituted or unsubstituted carboxyacyl;
wherein the dashed line represents an optional double bond between C20 and C29.

Preferred compounds useful in the present invention are those where R$_1$ is one of the substituents in Table 2, R$_2$ is hydrogen or one of the substituents in Table 12 and R$_3$ is hydrogen.

TABLE 2

Preferred Substituents

The most preferred compounds are 3-O-(3',3'-dimethylsuccinyl) betulinic acid, 3-O-(3',3'-dimethylsuccinyl) dihydrobetulinic acid, 3-O-(3',3'-dimethylsuccinyl) betulin, and 3-O-(3',3'-dimethylsuccinylglutaryl) dihydrobetulin.

Compounds useful in the methods of the present invention include derivatives of betulinic acid and betulin that are presented in U.S. Pat. Nos. 5,679,828 and 6,172,110 respectively, and in U.S. application Nos. 60/443,180 and 10/670, 797, which are herein incorporated by reference. Additional useful compounds include oleanolic acid derivatives disclosed by Zhu et al. (*Bioorg. Chem. Lett.* 11:3115-3118 (2001)); oleanolic acid and promolic acid derivatives disclosed by Kashiwada et al. (*J. Nat. Prod.* 61:1090-1095 (1998)); 3-O-acyl ursolic acid derivatives described by Kashiwada et al. (*J. Nat. Prod.* 63:1619-1622 (2000)); and 3-alkylamido-3-deoxy-betulinic acid derivatives, disclosed by Kashiwada et al. (*Chem. Pharm. Bull.* 48:1387-1390 (2000)). (All references incorporated by reference).

A particularly preferred compound is 3-O-(3',3'-dimethylsuccinyl) betulinic acid.

Reaction of betulinic acid and dihydrobetulinic acid with dimethylsuccinic anhydride produced a mixture of 3-O-(2', 2'-dimethylsuccinyl) and 3-O-(3',3'-dimethylsuccinyl)-betulinic acid and dihydrobetulinic acid, respectively. The mixtures were successfully separated by preparative scale HPLC yielding pure samples. The structures of these isomers were assigned by long-range $^1H$-$^{13}C$ COSY examinations.

The derivatives of betulinic acid and dihydrobetulinic acid of the present invention were all synthesized by refluxing a solution of betulinic acid or dihydrobetulinic acid, dimethylaminopyridine (1 equivalent mol), and an appropriate anhydride (2.5-10 equivalent mol) in anhydrous pyridine (5-10 mL). The reaction mixture was then diluted with ice water and extracted with $CHCl_3$. The organic layer was washed with water, dried over $MgSO_4$, and concentrated under reduced pressure. The residue was chromatographed using silica gel column or semi-preparative-scale HPLC to yield the product.

Preparation of 3-O-(3',3'-dimethylsuccinyl) betulinic acid: yield 70% (starting with 542 mg of betulinic acid); crystallization from MeOH gave colorless needles; mp 274°-276° C.; $[\alpha]_D^{19}$+23.5° (c=0.71), $CHCl_3$-MeOH [1:1]); Positive FABMS m/z 585 (M+H)$^+$; Negative FABMS m/z 583 (M–H)$^-$; HR-FABMS calcd for $C_{36}H_{57}O_6$ 585.4155, found m/z 585.4161; $^1H$ NMR (pyridine-$d_5$): 0.73, 0.92, 0.97, 1.01, 1.05 (each 3H, s; 4-$(CH_3)_2$, 8-$CH_3$, 10-$CH_3$, 14-$CH_3$), 1.55 (6H, s, 3'-$CH_3 \times 2$), 1.80 (3H, s, 20-$CH_3$), 2.89, 2.97 (each 1H, d, J=15.5 Hz, H-2'), 3.53 (1H, m, H-19), 4.76 (1H, dd, J=5.0, 11.5 Hz, H-3), 4.78, 4.95 (each 1H, br s, H-30).

3-O-(3',3'-dimethylsuccinyl) dihydrobetulinic acid: yield 24.5% (starting with 155.9 mg of dihydrobetulinic acid); crystallization from MeOH-$H_2O$ gave colorless needles; mp 291°-292° C.; $[\alpha]_D^{20}$–13.4° (c=1.1, $CHCl_3$-MeOH [1:1], $^1H$ NMR (pyridine-$d_5$): 0.85, 0.94 (each 3H, d, J=7.0 Hz; 20-$(CH_3)_2$), 0.75, 0.93, 0.97, 1.01, 1.03 (each 3H, s; 4-$(CH_3)_2$, 8-$CH_3$, 10-$CH_3$, 14-$CH_3$), 1.55 (6H, s; 3'-$CH_3 \times 2$), 2.89, 2.97 (each 1H, d, J=15.5 Hz; H-2'), 4.77 (1H, dd, J=5.0, 11.0 Hz, H-3); Anal. Calcd for $C_{36}H_{58}O_6 \cdot 5/2H_2O$: C, 68.43; H, 10.04. found C, 68.64; H, 9.78.

The synthesis of 3-O-(3',3'-dimethylglutaryl) betulinic acid was disclosed U.S. Pat. No. 5,679,828 as COMPOUND NO. 4.

3-O-(3',3'-dimethylglutaryl) dihydrobetulinic acid: yield 93.3% (starting with 100.5 mg of dihyrdobetulinic acid); crystallization from needles MeOH-$H_2O$ gave colorless needles; mp 287°-289° C.; $[\alpha]_D^{20}$–17.9° (c=0.5, $CHCl_3$-MeOH[1:1]); $^1H$-NMR (pyridine-$d_5$): 0.86, 0.93 (each 3H, d, J=6.5 Hz; 20-$(CH_3)_2$), 0.78, 0.92, 0.96, 1.02, 1.05 (each 3H, s; 4-$(CH_3)_2$, 8-$CH_3$, 10-$CH_3$, 14-$CH_3$), 1.38, 1.39 (each 3H, s; 3'-$CH_3 \times 2$), 2.78 (4H, m, $H_2$-2' and 4'), 4.76 (1H, dd, J=4.5, 11.5 Hz; H-3). Anal. Calcd for $C_{37}H_{60}O_6$: C, 73.96; H, 10.06. found C, 73.83; H, 10.10.

The synthesis for 3-O-diglycolyl-betulinic acid was disclosed in U.S. Pat. No. 5,679,828, as COMPOUND NO. 5.

3-O-diglycolyl-dihydrobetulinic acid: yield 79.2% (starting with 103.5 mg of dihydrobetulinic acid); an off-white amorphous powder; $[\alpha]_D^{20}$–9.8° (c=1.1, $CHCl_3$-MeOH[1:1]); $^1H$-NMR (pyridine-$d_5$): 0.79, 0.87 (each 3H, d, J=6.5 Hz; 20-$(CH_3)_2$), 0.87, 0.88, 0.91, 0.98, 1.01 (each 3H, s; 4-$(CH_3)_2$, 8-$CH_3$, 10-$CH_3$, 14-$CH_3$), 4.21, 4.23 (each 2H, s, $H_2$-2' and 4'), 4.57 (1H, dd, J=6.5, 10.0 Hz, H-3); Anal. Calcd for $C_{34}H_{54}O_7 \cdot 2H_2O$: C, 66.85; H, 9.57. found C, 67.21; H, 9.33.

The syntheses of 3-O-(3',3'-dimethylsuccinyl) betulin and 3-O-(3',3'-dimethylglutaryl) betulin were disclosed in U.S. application Ser. No. 10/670,797.

The method of inhibiting an HIV-1 replication in cells of an animal includes a compound of Formula I or Formula II, above, which is a derivative of betulinic acid, betulin, or dihydrobetulinic acid or dihydrobetulin and which includes the preferred substituents of Table 2. Preferred compounds include but are not limited to 3-O-(3',3'-dimethylsuccinyl) betulinic acid, 3-O-(3',3'-dimethylsuccinyl) betulin, 3-O-(3', 3'-dimethylglutaryl) betulin, methylsuccinyl) dihydrobetulinic acid, 3-O-(3',3'-dimethylglutaryl) betulinic acid, (3',3'-dimethylglutaryl) dihydrobetulinic acid, 3-O-diglycolyl-betulinic acid, and 3-O-diglycolyl-dihydrobetulinic acid.

The method disclosed herein, further comprises contacting said cells with one or more drugs selected from the group consisting of anti-viral agents, anti-fungal agents, anti-bacterial agents, anti-cancer agents, immunostimulating agents, and combinations thereof. The method may include the treatment of human blood products.

The invention may also be used in conjunction with a method of treating cancer comprising the administration to an animal of one or more anti-neoplastic agents, exposing an animal to a cancer cell-killing amount of radiation, or a combination of both.

The invention further includes a method for identifying compounds that inhibit HIV-1 replication in cells of an animal disclosed herein, said method comprising:
  a. contacting a Gag protein comprising a CA-SP1 cleavage site with a test compound;
  b. adding a labeled substance that selectively binds at or near the CA-SP1 cleavage site; and
  c. measuring the binding of the test compound at or near the CA-SP1 cleavage site.

Labeled substances or molecules include labeled antibodies or labeled DSB and the label includes an enzyme, fluorescent substance, chemiluminescent substance, horseradish peroxidase, alkaline phosphatase, biotin, avidin, electron dense substance, such as gold, osmium tetroxide, lead or uranyl acetate, and radioisotope, antibodies labeled with such substances of molecules or a combination thereof. The assays could include, but are not limited to ELISA, single and double sandwich techniques, immunodiffusion or immunoprecipitation techniques, as known in the art ("*Immunoassay Handbook*, $2^{nd}$ ed.," D. Wild, Nature Publishing Group, (2001)). Said methods of identifying also could include, but are not limited to Western blot assays, colorimetric assays, light and electron microscopic techniques, confocal microscopy, or other techniques known in the art.

A method of identifying compounds that inhibit HIV replication in cells of an animal further comprises:
  a. contacting a Gag protein comprising a wild-type CA-SP1 cleavage site, with HIV-1 protease in the presence of a test compound;
  b. separately, contacting a Gag protein comprising a mutant CA-SP1 cleavage site or a protein comprising an alternative protease cleavage site with HIV-1 protease in the presence of the test compound; and c. comparing the cleavage of the native wild-type Gag protein to the amount of cleavage of the mutant Gag protein or to the amount of cleavage of the peptide comprising an alternative protease cleavage site.

Step (b) above is performed as a control in order to eliminate compounds that might bind directly to, and therefore inhibit, the protease enzyme. The above method also includes the method wherein the wild-type CA-SP1, mutant CA-SP1 or alternative protease cleavage site is contained within a polypeptide fragment or recombinant peptide.

The method for identifying compounds that inhibit HIV-1 disclosed herein also, includes a method wherein said peptide or protein is labeled with a fluorescent moiety and a fluorescence quenching moiety, each bound to opposite sides of the CA-SP1 cleavage site, and wherein said detecting comprises measuring the signal from the fluorescent moiety, or wherein said peptide or protein is labeled with two fluorescent moieties, each bound to opposite sides of the CA-SP1 cleavage site, and wherein said detecting comprises measuring the transfer of fluorescent energy from one moiety to the other in the presence of the test compound and HIV-1 protease and comparing said transfer of fluorescent energy to that observed when the same procedure is applied to a peptide that comprises a sequence containing a mutation in the CA-SP1 cleavage site or that comprises a sequence containing another cleavage site. Examples of fluorescence-based assays of protease activity are well known in the art. In one such example, a protease substrate is labeled with green fluorescent dye molecules, which fluoresce when the substrate is cleaved by the protease enzyme (Molecular Probes, Protease Assay Kit).

The method of comparing the cleavage, above, also includes using a labeled antibody that selectively binds CA or SP1 in order to measure the extent to which the test compound inhibits CA-SP1 cleavage. The antibody can be labeled with a molecule selected from the group consisting of enzyme, fluorescent substance, chemiluminescent substance, horseradish peroxidase, alkaline phosphatase, biotin, avidin, electron dense substance, and radioisotope, or combinations thereof. The method also includes the use of an antibody to a specific epitope tag sequence to selectively detect p25 or SP1 into which the amino acid sequence for that epitope tag has been engineered according to standard methods in the art. As an example, the sequence of the FLAG epitope tag (Sigma-Aldrich) could be inserted into the p2 (SP1) region of Gag by oligonucleotide-directed mutagenesis of a Gag expression plasmid. The presence of the SP1 region in the cell-expressed protein could then be detected using commercially available anti-FLAG monoclonal antibodies (Sigma-Aldrich). (Hopp, T. P. *Biotechnology* 6: 1204-1210 (1988)).

The method also includes the addition of a compound to cells infected with HIV-1 and the detection of CA-SP1 cleavage products by lysing and analyzing the cells or the released virions. The method included in the invention can be performed using a western blot analysis of viral proteins and detecting p25 using an antibody that selectively binds p25 or wherein said mixture is analyzed by performing a gel electrophoresis of viral proteins and imaging of metabolically labeled proteins, or wherein the mixture is analyzed using immunoassays that use an antibody that selectively binds p25 or selectively binds SP1 to distinguish p25 from p24. For example, a microwell assay can be performed where p25 in detergent-solubilized virus is captured using an antibody selectively binds SP1 that is bound to the plastic multiple well plate. Following a washing step, bound p25 is detected using an antibody to p24 that is conjugated to an appropriate detection reagent (e.g. alkaline phosphatase for an enzyme-linked immunosorbent assay). Virus released by cells treated with compounds that act via this mechanism will have increased levels of p25 compared with untreated virions.

The disclosed method is drawn to an antibody that selectively binds p25, or an antibody that selectively binds SP1, which is labeled with a molecule selected from the group consisting of enzyme, fluorescent substance, chemiluminescent substance, horseradish peroxidase, alkaline phosphatase, biotin, avidin, electron dense substance, and radioisotope, or combinations thereof. The invention also includes the use of an antibody to a specific epitope tag sequence to selectively detect p25 or SP1 into which the amino acid sequence for that epitope tag has been engineered according to standard methods in the art.

"Infected cells," as used herein, includes cells infected naturally by membrane fusion and subsequent insertion of the viral genome into the cells, or transfection of the cells with viral genetic material through artificial means. These methods include, but are not limited to, calcium phosphate transfection, DEAE-dextran mediated transfection, microinjection, lipid-mediated transfection, electroporation or infection.

The invention may be practiced by infecting target cells in vitro with an infectious strain of HIV and in the presence of test compound, under appropriate culture conditions and for varying periods of time. Infected cells or supernatant fluid can be processed and loaded onto a polyacrylamide gel for the detection of virus levels, by methods that are well known in the art. Non-infected and non-treated cells can be used as negative and positive infection controls, respectively. Alternatively, the invention may be practiced by culturing the target cells in the presence of test compound prior to infecting the cells with an HIV strain.

The invention also includes a method for identifying compounds that inhibit HIV-1 replication in the cells of an animal, comprising:

a. contacting a test compound with wild-type virus isolates and separately with virus isolates resistant to 3-O-(3',3'-dimethylsuccinyl) betulinic acid; and b. selecting test compounds that are more active against the wild-type virus isolate compared with virus isolates that are resistant to 3-O-(3',3'-dimethylsuccinyl) betulinic acid.

This invention further includes a method for identifying compounds that act by any of the abovementioned mechanism, involving treating HIV-1 infected or transfected cells with a compound then analyzing the virus particles released by compound-treated cells by thin-sectioning and transmission electron microscopy, by standard methods well known in the art. A compound acts by the abovementioned mechanism if particles are detected that exhibit spherical condensed cores that are acentric with respect to the viral particle and a crescent-shaped electron-dense layer just inside the viral membrane.

For electron microscopic studies, infected cells or centrifuged virus pellets obtained from the supernatant fluid can be contacted with a fixative, such as glutaraldehyde or freshly-made paraformaldehyde, and/or osmium tetroxide or other electron microscopy compatible fixative that is known in the art. The virus from the supernatant fluid or the cells, is dehydrated and embedded in an electron-lucent polymer such as an epoxy resin or methacrylate, thin sectioned using an ultramicrotome, stained using electron dense stains such as uranyl acetate, and/or lead citrate, and viewed in a transmission electron microscope. Non-infected and non-treated cells can be used as negative and positive infection controls, respectively. Alternatively, the invention may be practiced by culturing the target cells in the presence of test compound prior to infecting the cells with an HIV strain. Maturation defects caused by the compounds of the present invention are determined by the presence of morphologically aberrant viral particles, compared with controls, as described herein.

For cell culture studies, the virus-infected cells may be observed for the formation of syncytia, or the supernatant may be tested for the presence of HIV particles. Virus present in the supernatant may be harvested to infect other naïve cultures to determine infectivity.

Also included in the invention, is a method of determining if an individual is infected with HIV-1, is susceptible to treatment by a compound that inhibits p25 processing, the method involves taking blood from the patient, genotyping the viral RNA and determining whether the viral RNA contains mutations in the CA-SP1 cleavage site.

The invention also includes a method for identifying compounds that act by the abovementioned mechanisms, involving testing by a combination of the methods disclosed herein.

HIV Gag protein and fragments thereof for use in the aforementioned assays may be expressed or synthesized using a variety of methods familiar to those skilled in the art. Gag can be produced in an in vitro transcription and translation system using a rabbit reticulocyte lysate. Gag expressed in this system has been shown to be processed sequentially in a pattern similar to that observed in infected cells (Pettit, S. C. et al. *J. Virol.* 76:10226-10233 (2002)). Moreover, Gag expressed by this method is capable of assembling into immature viral particles when fused to a heterologous type D retroviral cytoplasmic self-assembly domain (Sakalian, M. et al., *J. Virol.* 76:10811-10820 (2002)). The plasmid pDAB72, available from the NIH AIDS Reagent Program can be used for this purpose (Erickson-Viitanen, S. et al., *AIDS Res. Hum. Retroviruses.* 5:577-91 (1989); Sidhu M. K. et al., *Biotechniques,* 18:20, 22, 24 (1995)). Other in vitro transcription/translation systems based on wheat germ or bacterial lysates can also be used for this purpose. HIV Gag may also be expressed in transfected cells using a variety of commercially available expression vectors. The plasmid p55-GAG/GFP, available from the NIH AIDS Reagent Program, may be used to express an HIV Gag-green fluorescent protein fusion protein in mammalian cells for drug interaction studies (Sandefur, S. et al., *J. Virol.* 72:2723-2732 (1998)). This construct would permit the capture and purification of Gag fusion protein using GFP-specific monoclonal antibodies. In addition, Gag may be expressed in cells using recombinant viral vectors, such as those used in the vaccinia virus, adenovirus, or baculovirus systems. Gag can also expressed by infecting cells with HIV or by transfecting cells with proviral DNA. Finally, Gag may be expressed in yeast or bacterial cells transformed with the appropriate expression vectors.

In addition to Gag proteins expressed in cells or in vitro using cell lysates, peptides corresponding to various regions of Gag may be commercially synthesized from using standard peptide synthesis techniques.

The invention further encompasses compounds identified by the method of this invention and/or a compound which inhibits HIV-1 replication according to the methods of this invention and pharmaceutical compositions comprising one or more compounds as disclosed herein, or pharmaceutically acceptable salts, esters or prodrugs thereof, and pharmaceutically acceptable carriers.

Also included in the invention are compounds that are useful in the present invention, which include compounds of Formula I and Formula II, above. Preferred compounds include 3-O-(3',3'-dimethylsuccinyl) betulinic acid, 3-O-(3', 3'-dimethylsuccinyl) betulin, 3-O-(3',3'-dimethylglutaryl) betulin, 3-O-(3',3'-dimethylsuccinyl) dihydrobetulinic acid, 3-O-(3',3'-dimethylglutaryl) betulinic acid, (3',3'-dimethylglutaryl) dihydrobetulinic acid, 3-O-diglycolyl-betulinic acid, 3-O-diglycolyl-dihydrobetulinic acid, and any combination thereof.

Also, included within the scope of the present invention are the non-toxic pharmaceutically acceptable salts of the compounds of the present invention. These salts can be prepared in situ during the final isolation and purification of the compounds or by separately reacting the purified compound in its free acid form with a suitable organic or inorganic base and isolating the salt thus formed. These may include cations based on the alkali and alkali earth metals, such as sodium, lithium, potassium, calcium, magnesium, and the like, as well as nontoxic ammonium, quaternary ammonium and amine cations including, but not limited to ammonium, tetra-methylammonium, tetraethylammonium, methylamine, dimethylamine, trimethylamine, ethylamine, N-methyl-glucamine and the like.

Compounds of Formulas I and II according to the present invention have been found to possess anti-retroviral, particularly anti-HIV, activity. The salts and other formulations of the present invention are expected to have improved water solubility, and enhanced oral bioavailability. Also, due to the improved water solubility, it will be easier to formulate the salts of the present invention into pharmaceutical preparations. Further, compounds of Formula I and II according to the present invention are expected to have improved biodistribution properties.

This invention also includes a pharmaceutical composition comprising a compound that inhibits processing of the viral Gag p25 protein (CA-SP1) to p24 (CA), but has no significant effect on other Gag processing steps, or that inhibits the maturation of virus particles released from treated infected cells, such as the compounds of Formula I and II. The invention includes a pharmaceutical composition comprising one or more compounds disclosed herein, or pharmaceutically acceptable salts, esters or prodrugs thereof, and pharmaceutically acceptable carriers, wherein said compound is of Formula I or II above, or preferably, wherein said compound is selected from the group consisting of 3-O-(3',3'-dimethylsuccinyl) betulinic acid, 3-O-(3',3'-dimethylsuccinyl) betulin, 3-O-(3',3'-dimethylglutaryl) betulin, 3-O-(3',3'-dimethylsuccinyl) dihydrobetulinic acid, 3-O-(3',3'-dimethylglutaryl) betulinic acid, (3',3'-dimethylglutaryl) dihydrobetulinic acid, 3-O-diglycolyl-betulinic acid, and 3-O-diglycolyl-dihydrobetulinic acid. The pharmaceutical compositions according to the invention, further comprise one or more drugs selected from an anti-viral agent, anti-fungal agent, anti-cancer agent or an immunostimulating agent.

Pharmaceutical compositions of the present invention can comprise at least one of the compounds of Formula I or II disclosed herein. Pharmaceutical compositions according to the present invention can also further comprise other anti-viral agents such as, but not limited to, AZT (zidovudine, RETROVIR®, GlaxoSmithKline), 3TC (lamivudine, EPIVIR®, GlaxoSmithKline), AZT+3TC (COMBIVIR®, GlaxoSmithKline), ddI (didanosine, VIDEX®, Bristol-Myers Squibb), ddC (zalcitabine, HIVID®, Hoffmann-La Roche), D4T (stavudine, ZERIT®, Bristol-Myers Squibb), abacavir (ZIAGEN®, GlaxoSmithKline), nevirapine (VIRAMUNE®, Boehringer Ingelheim), delavirdine (Pfizer), efavirenz (SUSTIVA®, DuPont Pharmaceuticals), saquinavir (INVIRASE®, FORTOVASE®, Hoffmann-La Roche), ritonavir (NORVIR®, Abbott Laboratories), indinavir (CRIXIVAN®, Merck and Company), nelfinavir (VI- RACEPT®, Pfizer), amprenavir (AGENERASE®, GlaxoSmithKline), adefovir (PREVEON®, HEPSERA®, Gilead Sciences), atazanavir (Bristol-Myers Squibb), and hydroxyurea (HYDREA®, Bristol-Meyers Squibb), or any other antiretroviral drugs or antibodies in combination with each other, or associated with a biologically based therapeutic, such as, for example, gp41-derived peptides enfuvirtide (FUZEON®, Roche and Trimeris) and T-1249, or soluble CD4, antibodies to CD4, and conjugates of CD4 or anti-CD4, or as additionally presented herein.

Additional suitable antiviral agents for optimal use with one of the compounds of Formula I or II of the present invention can include, but are not limited to, AL-721 (lipid mixture) manufactured by Ethigen Corporation and Matrix Research Laboratories; amphotericin B (FUNGIZONE®; Ampligen (mismatched RNA) developed by DuPont/HEM Research; anti-AIDS antibody (Nisshon Food); 1 AS-101 (heavy metal based immunostimulant); BETASERON® (β-interferon, Triton Biosciences); butylated hydroxytoluene; Carrosyn (polymannoacetate); Castanospermine; Contracan (stearic acid derivative); Creme Pharmatex (containing benzalkonium chloride) manufactured by Pharmalec; CS-87 (5-unsubstituted derivative of zidovudine); penciclovir (DENAVIR® Novartis); famciclovir (FAMVIR® Novartis); acyclovir (ZOVIRAX® GlaxoSmithKline); HPMPC (cytofovir, VISTIDE® Gilead); DHPG, (ganciclovir, CYTOVENE®, Roche Pharmaceuticals); dextran sulfate; D-penicillamine (3-mercapto-D-valine) manufactured by Carter-Wallace and Degussa Pharmaceutical; FOSCARNET® (trisodium phosphonoformate; Astra AB); fusidic acid manufactured by Leo Lovens; glycyrrhizin (a constituent of licorice root); HPA-23 (ammonium-21-tungsto-9-antimonate; Rhone-Poulenc Sante); human immune virus antiviral developed by Porton Products International; ORNIDYL® (eflornithine; Merrell-Dow); nonoxynol; pentamidine isethionate (PENTAM-300) manufactured by Lypho Med; Peptide T (octapeptide sequence) manufactured by Peninsula Laboratories; Phenyloin (Pfizer); INH or isoniazid; ribavirin (RIFADIN®, Aventis); (VIRAZOLE®, Valeant Pharmaceuticals); rifabutin, ansamycin (MYCOBUTIN® Pfizer); CD4-IgG2 (Progenies Pharmaceuticals) or other CD4-containing or CD4-based molecules; Trimetrexate manufactured by Pfizer; SK-818 (germanium-derived antiviral) manufactured by Sanwa Kagaku; suramin and analogues thereof manufactured by Miles Pharmaceuticals; UA001 manufactured by Ueno Fine Chemicals Industry; and WELLFERON® (α-interferon, GlaxoSmithKline).

Pharmaceutical compositions of the present invention can also further comprise immunomodulators. Suitable immunomodulators for optional use with a betulinic acid or betulin derivative of the present invention in accordance with the present invention can include, but are not limited to: ABPP (Bropririmine); Ampligen (mismatched RNA) DuPont/HEM Research; anti-human interferon-α-antibody (Advance Biotherapy and Concepts); anti-AIDS antibody (Nisshon Food); AS-101 (heavy metal based immunostimulant; ascorbic acid and derivatives thereof; interferon-β; Ciamexon (Boehringer-Mannheim); cyclosporin; cimetidine; CL-246,738 (American Cyanamid); colony stimulating factors, including GM-CSF (Sandoz, Genetics Institute); dinitrochlorobenzene; HE2000 (Hollis-Eden Pharmaceuticals); inteferon-γ; glucan; hyperimmune gamma-globulin (Bayer); IMREG-1 (leukocyte dialyzate) and IMREG-2 (IMREG Corp.); immuthiol (sodium diethylthiocarbamate) (Institut Merieux); interleukin-1 (Cetus Corporation, Hoffmann-LaRoche; Immunex), interleukin-2 (IL-2) (Chiron Corporation), isoprinosine (inosine pranobex), Krestin (Sankyo), LC-9018 (Yakult), lentinan (Ajinomoto/Yamanouchi); LF-1695 (Fournier), methionine-enkephalin (TNI Pharmaceuticals; Sigma Chemicals), Minophagen C; muramyl tripeptide, MTP-PE (Ciba-Geigy), naltrexone (TREXAN® DuPont); Neutropin, RNA immunomodulator (Nippon Shingaku), REMUNE® (Immune Response Corporation), RETICULOSE® (Advanced Viral Research Corporation), shosaikoto, ginseng, thymic humoral factor, TP-05 (Thymopentin, Ortho Pharmaceuticals), thymosin factor 5, thymosin 1 (ZYDAXIN®, SciClone), thymostimulin, TNF (tumor necrosis factor Genentech), and vitamin preparations.

Pharmaceutical compositions of the present invention can also further comprise anti-cancer therapeutic agents. Suitable anti-cancer therapeutic agents for optional use include an anti-cancer composition effective to inhibit neoplasia comprising a compound, or a pharmaceutically acceptable salt or prodrug of said anti-cancer agent, which can be used for combination therapy include, but are not limited to alkylating agents, such as busulfan, cis-platin, mitomycin C, and carboplatin antimitotic agents, such as colchicine, vinblastine, taxols, such as paclitaxel (TAXOL®, Bristol-Meyers Squibb) docetaxel (TAXOTERE®, Aventis), topo I inhibitors, such as camptothecin, irinotecan and topotecan (HYCAMTIN®, SmithKline Beecham), topo II inhibitors, such as doxorubicin, daunorubicin and etoposides such as VP16; RNA/DNA antimetabolites, such as 5-azacytidine, 5-fluorouracil and methotrexate, DNA antimetabolites, such as 5-fluoro-2'-deoxy-uridine, ara-C, hydroxyurea, thioguanine, and antibodies, such as trastuzumab (HERCEPTIN®, Genentech), and rituximab (RITUXAN®, Genentech and Idec Pharmaceuticals), melphalan, chlorambucil, cyclophosamide, ifosfamide, vincristine, mitoguazone, epirubicin, aclarubicin, bleomycin, mitoxantrone, elliptinium, fludarabine, octreotide, retinoic acid, tamoxifen, alanosine, and combinations thereof.

The invention further provides methods for providing anti-bacterial therapeutics, anti-parasitic therapeutics, and anti-fungal therapeutics, for use in combination with the compounds of the invention and pharmaceutically-acceptable salts thereof. Examples of anti-bacterial therapeutics include compounds such as penicillins, ampicillin, amoxicillin, cyclacillin, epicillin, methicillin, nafcillin, oxacillin, cloxacillin, dicloxacillin, flucloxacillin, carbenicillin, cephalexin, cepharadine, cefadoxil, cefaclor, cefoxitin, cefotaxime, ceftizoxime, cefinenoxine, ceftriaxone, moxalactam, imipenem, clavulanate, timentin, sulbactam, erythromycin, neomycin, gentamycin, streptomycin, metronidazole, chloramphenicol, clindamycin, lincomycin, quinolones, rifampin, sulfonamides, bacitracin, polymyxin B, vancomycin, doxycycline, methacycline, minocycline, tetracycline, amphotericin B, cycloserine, ciprofloxacin, norfloxacin, isoniazid, ethambutol, and nalidixic acid, as well as derivatives and altered forms of each of these compounds.

Examples of anti-parasitic therapeutics include bithionol, diethylcarbamazine citrate, mebendazole, metrifonate, niclosamine, niridazole, oxamniquine and other quinine derivatives, piperazine citrate, praziquantel, pyrantel pamoate and thiabendazole, as well as derivatives and altered forms of each of these compounds.

Examples of anti-fungal therapeutics include amphotericin B, clotrimazole, econazole nitrate, flucytosine, griseofulvin, ketoconazole and miconazole, as well as derivatives and altered forms of each of these compounds. Anti-fungal compounds also include aculeacin A and papulocandin B.

The term "prodrug", as used herein refers to compounds which undergo biotransformation prior to exhibiting their pharmacological effects. The chemical modification of drugs to overcome pharmaceutical problems has also been termed "drug latentiation." Drug latentiation is the chemical modification of a biologically active compound to form a new compound which upon in vivo enzymatic attack will liberate the parent compound. The chemical alterations of the parent compound are such that the change in physicochemical properties will affect the absorption, distribution and enzymatic metabolism. The definition of drug latentiation has also been extended to include nonenzymatic regeneration of the parent compound. Regeneration takes place as a consequence of hydrolytic, dissociative, and other reactions not necessarily enzyme mediated. The terms "prodrugs," "latentiated drugs," and "bioreversible derivatives" are used interchangeably. By inference, latentiation implies a time lag element or time component involved in regenerating the bioactive parent molecule in vivo. The term "prodrug" is general in that it includes latentiated drug derivatives as well as those substances which are converted after administration to the actual substance. The term "prodrug" is a generic term for agents which undergo biotransformation prior to exhibiting their pharmacological actions.

The preferred animal subject of the present invention is a mammal. By the term "mammal" is meant an individual belonging to the class Mammalia. The invention is particularly useful in the treatment of human patients.

The term "treating" means the administering to subjects a compound of Formula I or II or a compound identified by one or more assays within the present invention, for purposes which can include prevention, amelioration, or cure of a retroviral-related pathology. Said compounds for treating a subject that are identified by one or more assays within the present inventions are identified as compounds which have the ability to disrupt Gag processing, described herein.

The term "inhibits the interaction" as used herein, means preventing, or reducing the rate of, direct or indirect association of one or more molecules, peptides, proteins, enzymes, or receptors; or preventing or reducing the normal activity of one or more molecules, peptides, proteins, enzymes or receptors.

Medicaments are considered to be provided "in combination" with one another if they are provided to the patient concurrently or if the time between the administration of each medicament is such as to permit an overlap of biological activity.

In one preferred embodiment, at least one compound of Formula I or II above comprises a single pharmaceutical composition.

Pharmaceutical compositions for administration according to the present invention can comprise at least one compound of Formula I or II above or compounds identified by one or more assays within the present invention. Said compounds for treating a subject that are identified by one or more assays within the present inventions are identified as compounds which have the ability to disrupt Gag processing, described herein. The compounds according to the present invention are further included in a pharmaceutically acceptable form optionally combined with a pharmaceutically acceptable carrier. These compositions can be administered by any means that achieve their intended purposes. Amounts and regimens for the administration of a compound of Formula I or II according to the present invention can be determined readily by those with ordinary skill in the clinical art of treating a retroviral pathology.

For example, administration can be by parenteral, such as subcutaneous, intravenous, intramuscular, intraperitoneal, transdermal, transmucosal, ocular, rectal, intravaginal, or buccal routes. Alternatively, or concurrently, administration can be by the oral route. The administration may be as an oral or nasal spray, or topically, such as powders, ointments, drops or a patch. The dosage administered depends upon the age, health and weight of the recipient, type of previous or concurrent treatment, if any, frequency of treatment, and the nature of the effect desired.

Compositions within the scope of this invention include all compositions comprising at least one compound of Formula I or II above according to the present invention in an amount effective to achieve its intended purpose. While individual needs vary, determination of optimal ranges of effective amounts of each component is within the skill of the art. Typical dosages comprise about 0.1 to about 100 mg/kg body weight. The preferred dosages comprise about 1 to about 100 mg/kg body weight of the active ingredient. The most preferred dosages comprise about 5 to about 50 mg/kg body weight.

Administration of a compound of the present invention can also optionally include previous, concurrent, subsequent or adjunctive therapy using immune system boosters or immunomodulators. In addition to the pharmacologically active compounds, a pharmaceutical composition of the present invention can also contain suitable pharmaceutically acceptable carriers comprising excipients and auxiliaries which facilitate processing of the active compounds into preparations which can be used pharmaceutically. Preferably, the preparations, particularly those preparations which can be administered orally and which can be used for the preferred type of administration, such as tablets, dragees, and capsules, and also preparations which can be administered rectally, such as suppositories, as well as suitable solutions for administration by injection or orally, contain from about 0.01 to 99 percent, preferably from about 20 to 75 percent of active compound(s), together with the excipient.

Pharmaceutical preparations of the present invention are manufactured in a manner which is itself known, for example, by means of conventional mixing, granulating, dragee-making, dissolving, or lyophilizing processes. Thus, pharmaceutical preparations for oral use can be obtained by combining the active compounds with solid excipients, optionally grinding the resulting mixture, and processing the mixture of granules, after adding suitable auxiliaries, if desired or necessary, to obtain tablets or dragee cores.

Suitable excipients are, e.g., fillers such as saccharide, for example, lactose or sucrose, mannitol or sorbitol; cellulose preparations and/or calcium phosphates, such as tricalcium phosphate or calcium hydrogen phosphate; as well as binders such as starch paste, using, for example, maize starch, wheat starch, rice starch, potato starch, gelatin, tragacanth, cellulose, methyl cellulose, hydroxypropylmethylcellulose, sodium carboxymethylcellulose, and/or polyvinyl pyrrolidone. If desired, disintegrating agents can be added such as the above-mentioned starches and also carboxymethyl starch, cross-linked polyvinyl pyrrolidone, agar, or alginic acid or a salt thereof, such as sodium alginate. Auxiliaries are, above all, flow-regulating agents and lubricants, for example, silica, talc, stearic acid or salts thereof, such as magnesium stearate or calcium stearate, and/or polyethylene glycol. Dragee cores are provided with suitable coatings which, if desired, are resistant to gastric juices. For this purpose, concentrated saccharide solutions can be used, which can optionally contain gum arabic, talc, polyvinyl pyrrolidone, polyethylene glycol and/or titanium dioxide, lacquer solutions and suitable organic solvents or solvent mixtures. In order to produce coatings resistant to gastric juices, solutions of suitable cellulose preparations such as acetylcellulose phthalate or hydroxypropylmethyl cellulose phthalate are used. Dyestuffs or pigments can be added to the tablets or dragee coatings, for example, for identification or in order to characterize combinations of active compound doses.

Other pharmaceutical preparations which an be used orally include push-fit capsules made of gelatin, as well as soft, sealed capsules made of gelatin and a plasticizer such as glycerol or sorbitol. The push-fit capsules can contain the active compounds in the form of granules which can be mixed with fillers such as lactose, binders such as starches, and/or lubricants such as talc or magnesium stearate and, optionally, stabilizers. In soft capsules, the active compounds are preferably dissolved or suspended in suitable liquids, such as fatty oils or liquid paraffin. In addition, stabilizers can be added.

Possible pharmaceutical preparations which can be used rectally include, for example, suppositories which consist of a combination of the active compounds with a suppository base. Suitable suppository bases are, for example, natural or synthetic triglycerides, or paraffin hydrocarbons. In addition, it is also possible to use gelatin rectal capsules which consist of a combination of the active compounds with a base. Possible base materials include, for example, liquid triglycerides, polyethylene glycols, or paraffin hydrocarbons.

Suitable formulations for parenteral administration include aqueous solutions of the active compounds in water-soluble form, for example, water-soluble salts. In addition, suspensions of the active compounds as appropriate oily injection suspensions can be administered. Suitable lipophilic solvents or vehicles include fatty oils, such as sesame oil, or synthetic fatty acid esters, such as ethyl oleate, triglycerides or glycol-400. Aqueous injection suspensions that can contain substances which increase the viscosity of the suspension include, for example, sodium carboxymethyl cellulose, sorbitol, and/or dextran. Optionally, the suspension can also contain stabilizers.

Liquid dosage forms for oral administration include pharmaceutically acceptable emulsions, solutions, suspensions, syrups, and elixirs. In addition to the active compounds, the liquid dosage forms may contain inert diluents commonly used in the art such as, for example, water or other solvents, solubilizing agents and emulsifiers such as, for example, water or other solvents, solubilizing agents and emulsifiers such as ethyl alcohol, isopropyl alcohol, ethyl carbonate, ethyl acetate, benzyl alcohol, benzyl benzoate, propylene glycol, 1,3-butylene glycol, dimethyl formamide, oils such as cottonseed, groundnut, corn, germ, olive, castor, and sesame oils, glycerol, tetrahydrofurfuryl alcohol, polyethylene glycols and fatty acid esters of sorbitan, and mixtures thereof.

Suspensions, in addition to the active compounds, may contain suspending agents as, for example, ethoxylated isostearyl alcohols, polyoxyethylene sorbitol and sorbitan esters, cellulose, microcrystalline cellulose, aluminum metahydroxide, bentonite, agar-agar, and tragacanth, and combinations thereof.

Pharmaceutical compositions for topical administration include formulations appropriate for administration to the skin, mucosa, surfaces of the lung or eye. Compositions may be prepared as a pressurized or non-pressurized dry powder, liquid or suspension. The active ingredients in non-pressurized powdered formulations may be admixed in a finely divided form in a pharmaceutically-acceptable inert carrier, including but not limited to mannitol, fructose, dextrose, sucrose, lactose, saccharin or other sugars or sweeteners.

The pressurized composition may contain a compressed gas, such as nitrogen, or a liquefied gas propellant. The propellant may also contain a surface-active ingredient, which may be a liquid or solid non-ionic or anionic agent. The anionic agent may be in the form of a sodium salt.

A formulation for use in the eye would comprise a pharmaceutically acceptable ophthalmic carrier, such as an ointment, oils, such as vegetable oils, or an encapsulating material. The regions of the eye to be treated include the corneal region, or internal regions such as the iris, lens, ciliary body, anterior chamber, posterior chamber, aqueous humor, vitreous humor, choroid or retina.

Compositions for rectal administration may be in the form of suppositories. Compositions for use in the vagina may be in the form of suppositories, creams, foams, or in-dwelling vaginal inserts.

The compositions may be administered in the form of liposomes. Liposomes may be made from phospholipids, phosphatidyl cholines (lecithins) or other lipoidal compounds, natural or synthetic, as known in the art. Any non-toxic, pharmacologically acceptable lipid capable of forming liposomes may be used. The liposomes may be multilamellar or mono-lamellar.

A pharmaceutical formulation for systemic administration according to the invention can be formulated for enteral, parenteral or topical administration. Indeed, all three types of formulation can be used simultaneously to achieve systemic administration of the active ingredient.

Suitable formulations for oral administration include hard or soft gelatin capsules, dragees, pills, tablets, including coated tablets, elixirs, suspensions, syrups or inhalations and controlled release forms thereof.

The compounds of Formula I or II above or compounds identified by one or more assays within the present invention and have the ability to disrupt Gag processing, can also be administered in the form of an implant when compounded with a biodegradable slow-release carrier. Alternatively, the compounds of the present invention can be formulated as a transdermal patch for continuous release of the active ingredient.

The following examples are illustrative only and are not intended to limit the scope of the invention as defined by the appended claims. It will be apparent to those skilled in the art that various modifications and variations can be made in the methods of the present invention without departing from the spirit and scope of the invention. Thus, it is intended that the present invention covers the modifications and variations of this invention provided they come within the scope of the appended claims and their equivalents.

EXAMPLES

Example 1

Anti-Viral Activity Against Primary HIV-1 Isolates

A robust virus inhibition assay was used to evaluate the anti-viral activity of DSB against primary HIV-1 isolates propagated in PMBC. Briefly, serial dilutions of DSB were made in medium into 96-well tissue culture plates. 25-250 $TCID_{50}$ of virus and $5\times10^5$ PHA-stimulated PBMCs were added to each well. On days 1, 3 and 5 post-infection, media was removed from each well and replaced with fresh media containing DSB at the appropriate concentration. On day 7 post-infection, culture supernatant was removed from each well for p24 detection of virus replication and 50% inhibitory concentrations ($IC_{50}$) were calculated by standard methods.

Table 3 shows the potent anti-viral activity of DSB against a panel of primary HIV-1 isolates. DSB exhibits levels of activity similar to approved drugs that were tested in parallel. Importantly, the activity of DSB was not restricted by co-receptor usage.

TABLE 3

Table 3: Inhibitory activity ($IC_{50}$) of DSB and two approved drugs against a panel of primary Clade B HIV-1 isolates. Clinical HIV-1 isolates denoted by * were isolated at Panacos. All other virus isolates were obtained from the NIH AIDS Reference Repository.

| Virus Isolate # | Co-Receptor usage | $IC_{50}$ (nM) DSB | AZT | Nevirapine |
|---|---|---|---|---|
| BZ167 | X4 | 4.0 | 2.2 | 31.2 |
| 92HT599 | X4 | 9.8 | 5.8 | 25.3 |
| US1 | R5 | 5.6 | 0.9 | 22.1 |
| 19101N* | R5 | 3.8 | 2.4 | 59.4 |
| 3401N* | R5/X4 | 12.0 | 17.5 | 32.1 |
| 92US723 | R5/X4 | 4.6 | 1.2 | 26.8 |
| 22101N* | R5/X4 | 2.6 | 0.9 | 4.9 |
| Mean | | 6.1 | 4.4 | 28.8 |

Note:
R5 and X4 refer to the chemokine receptors CCR5 and CXCR4 respectively.

Toxicity of DSB was analyzed by incubating with PHA-stimulated PBMC for 7 days at a range of concentrations, then determining cell viability using the XTT method. The 50% cytotoxic concentration was >30 μM, corresponding to an in vitro therapeutic index of approximately 5000.

Example 2

Anti-Viral Activity of DSB Against Drug Resistant HIV-1 Isolates

The activity of DSB was tested against a panel of HIV-1 isolates resistant to approved drugs. These viruses were obtained from the NIH AIDS Research and Reference Reagent Program. Assays were performed using virus propagated in PBMCs with a p24 endpoint (above), or using cell line targets (MT-2 cells) and a cell killing endpoint. The MT-2 assay format was as follows. Serial dilutions of DSB, or each approved drug, were prepared in 96 well plates. To each sample well was added media containing MT-2 cells at $3 \times 10^5$ cells/mL and virus inoculum at a concentration necessary to result in 80% killing of the cell targets at 5 days post-infection (PI). On day 5 post-infection, virus-induced cell killing was determined by the XTT method and the inhibitory activity of the compound was determined.

Table 4 shows the potent anti-viral activity of DSB against a panel of drug-resistant HIV-1 isolates. The results were not significantly different from those obtained with the panel of wild-type isolates (Table 3), demonstrating that DSB retains its activity against virus strains resistant to all of the major classes of approved drugs.

TABLE 4

Table 4: Inhibitory activity (nM $IC_{50}$) of DSB against a panel of drug resistant HIV-1 isolates. Assays were done in fresh PBMC with a p24 endpoint except for the NNRTI-resistant isolates that were performed in MT-2 cells with a cell viability (XTT) endpoint.

| Virus Isolate # | Mutation(s) | Co-Receptor usage | $IC_{50}$ (nM) DSB | AZT | Nevirapine | Indinavir |
|---|---|---|---|---|---|---|
| NRTI-resistant | | | | | | |
| 1 | K70R T215Y/F | R5/X4 | 4.4 | 86.4 (54X)* | ND | 9.8 |
| 2 | K70R T215Y/F | R5/X4 | 4.2 | 63.4 (40X) | ND | 6.1 |
| NNRTI-resistant | | | | | | |
| 3 | Y181C | X4 | 1.0 | 5.1 | >3800 (>177X) | 2.5 |
| 4 | K103N Y181C | X4 | 1.3 | 2.0 | 2630 (122X) | 4.5 |
| Protease-resistant | | | | | | |
| 5 | V82A | X4 | 5.6 | 13.1 | ND | 39.7 (12X) |
| 6 | I84V | X4 | 5.5 | 14.4 | ND | 32.7 (10X) |
| 7 | L10R/M46I/ L63P/V82T/I84V | X4 | 12.9 | 3.5 | ND | 72.5 (23X) |

*Fold Resistance.

Note:
R5 and X4 refer to the chemokine receptors CCR5 and CXCR4 respectively.

Example 3

DSB Inhibits HIV-1 Replication at a Late Step in the Virus Life Cycle

To distinguish the inhibitory activity of DSB against early and late replication targets, a multinuclear activation of a galactosidase indicator (MAGI) assay was used. In this assay, the targets are HeLa cells stably expressing CD4, CXCR4, CCR5 and a reporter construct consisting of the – galactosidase gene (modified to localize to the nucleus) driven by a truncated HIV-1 LTR. Infection of these cells results in expression of Tat that drives activation of the β-galactosidase reporter gene. Expression of β-galactosidase in infected cells is detected using the chromogenic substrate X-gal. As shown in Table 5, the entry inhibitor T-20, the NRTI AZT and the NNRTI nevirapine caused significant reductions in β-galactosidase gene expression in HIV-1 infected MAGI cells due to their ability to disrupt early steps in viral replication that affect Tat protein expression. In contrast, the protease inhibitor indinavir targets a late step in virus replication (following Tat expression) and does not prevent β-galactosidase gene expression in this system. Similar results were obtained with DSB as with indinavir, indicating that DSB blocks virus replication at a time point following the completion of proviral DNA integration and synthesis of the viral transactivating protein (Table 5).

TABLE 5

Table 5: Effect of DSB and inhibitors of entry (the gp41 peptide T-20), RT (AZT and Nevirapine) and protease (indinavir) on expression of b-galactosidase in HIV-1 infected MAGI cells. The DMSO control contained no drug.

| Inhibitor | DMSO | T-20 | AZT | Nevirapine | Indinavir | DSB |
|---|---|---|---|---|---|---|
| % Decrease (β-galactosidase expression) | 0 | 98 | 82 | 85 | 10 | 12 |

Kanamoto et al. (*Antimicrob. Agents Chemother.*, April; 45(4):1225-30, (2002)) have also reported that DSB acts at a late step in HIV replication. However, they reported that the compound inhibits release of virus from chronically-infected cells. In contrast, our data using a variety of experimental systems indicate that DSB does not have a significant effect on virus release (e.g. Example 6).

Example 4

DSB does not Inhibit HIV-1 Protease Activity

We had previously determined that DSB had no effect on HIV-1 protease function using a cell-free fluorometric assay that characterized enzyme activity by following the cleavage of a synthetic peptide substrate. The results of these experiments indicated that at concentrations up to 50 µg/mL that DSB had no effect on protease function. As a result of the observation that DSB blocks virus replication at a late step, studies were also performed using a recombinant form of the Gag protein, which is a more relevant system than the synthetic peptide substrate used in the initial assays. The use of the recombinant Gag protein as substrate resulted in a similar experimental outcome. In these experiments DSB did not disrupt protease-mediated Gag protein processing at concentrations as high as 50 µg/mL. In contrast, as expected, the protease inhibitor indinavir blocked Gag protein processing at 5 µg/mL (FIG. 1).

Example 5

Figure 2:
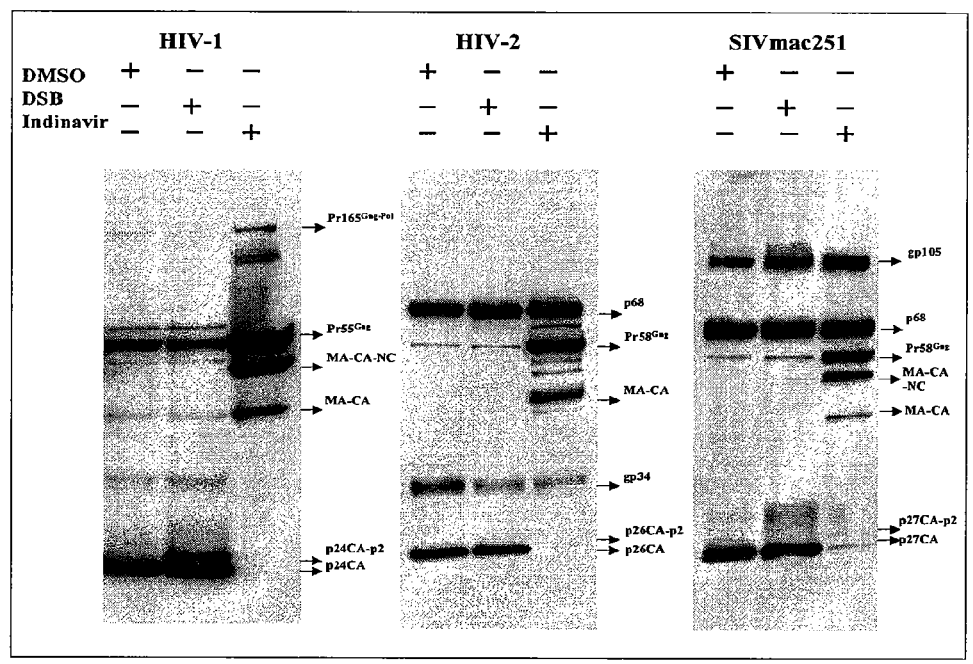

DSB Causes a Defect in the Final Step of Gag Processing (CA-SP1 Cleavage) that has been Associated with Viral Maturation Defects In order to better define DSB's mechanism of action, a detailed examination was undertaken of the virus produced from HIV-1-infected cell lines treated with DSB. Briefly, H9 cells chronically infected with the HIV-1$_{IIIB}$ isolate were treated with DSB at 1 µg/mL for a period of 48 hrs. Indinavir was used as a control. At the 48 hr time-point, spent media was removed and fresh media containing compound was added. At 24, 48 and 72 hrs post fresh compound addition, both cells and supernatant were recovered for analysis. The level of virus in the culture supernatant was determined and western blots were used to characterize viral protein production in both cell-associated and cell-free virus. As observed in previous experiments, DSB did not cause a significant reduction in the amount of virus produced by chronically infected H9 cells, however, there was a defect in Gag processing in both cell-associated and cell-free virus. This defect took the form of an additional band in the western blots corresponding to p25 (FIG. 2). This p25 band results from the incomplete processing of the capsid CA-SP1 precursor. DSB treatment of HIV-2 and SW chronically infected cell lines exhibited normal Gag processing consistent with the observed lack of antiviral activity against these viruses. The Gag processing defect seen in the presence of DSB is completely distinct from that observed with the protease inhibitor indinavir (FIG. 2). As discussed above, mutations at the p25 to p24 cleavage site that prevent processing are associated with defects in viral maturation and infectivity (Wiegers K. et al., *J. Virol.* 72:2846-54 (1998)).

As previously discussed (C. T. Wild et al., *XIV Int. AIDS Conf.* Barcelona, Spain, Abstract MoPeA3030, (July 2002)), abnormal p25 to p24 processing is also seen in other maturation budding defects. These include mutations in the Gag late domain (PTAP) or defects in TSG-101 mediated viral assembly that disrupt budding (Garrus, J. E et al., *Cell*, 107:55-65, (2001); Demirov, D. G. et al., *J. Virology* 76:105-117, (2002)). However, these mutations cause inhibition of virus release, while DSB treatment does not have a significant effect on virus release. The morphology of these maturation/budding mutants is also quite distinct from that following DSB-treatment (see Example 6).

In addition, mutations that interfere with viral RNA dimerization and lead to the production of immature virus with defective core structures give a similar Gag processing phenotype (Liang, C. et al., *J. Virology*, 73:6147-6151, (1999)). However, in those cases RNA incorporation is inhibited and the morphology of particles released is distinct from those following DSB treatment (see Example 6).

Example 6

DSB Treatment Effects HIV-1 Maturation as Determined by Electron Microscopy (EM)

It has been demonstrated that mutations in HIV-1 Gag that disrupt p25 to p24 processing give rise to non-infectious viral particles characterized by an internal morphology distinct from normal virus (Wiegers K. et al., *J. Virol.* 72:2846-54

(1998)). To determine if virus generated in the presence of DSB exhibited this distinct morphology the following experiment was carried out.

Figure 3:
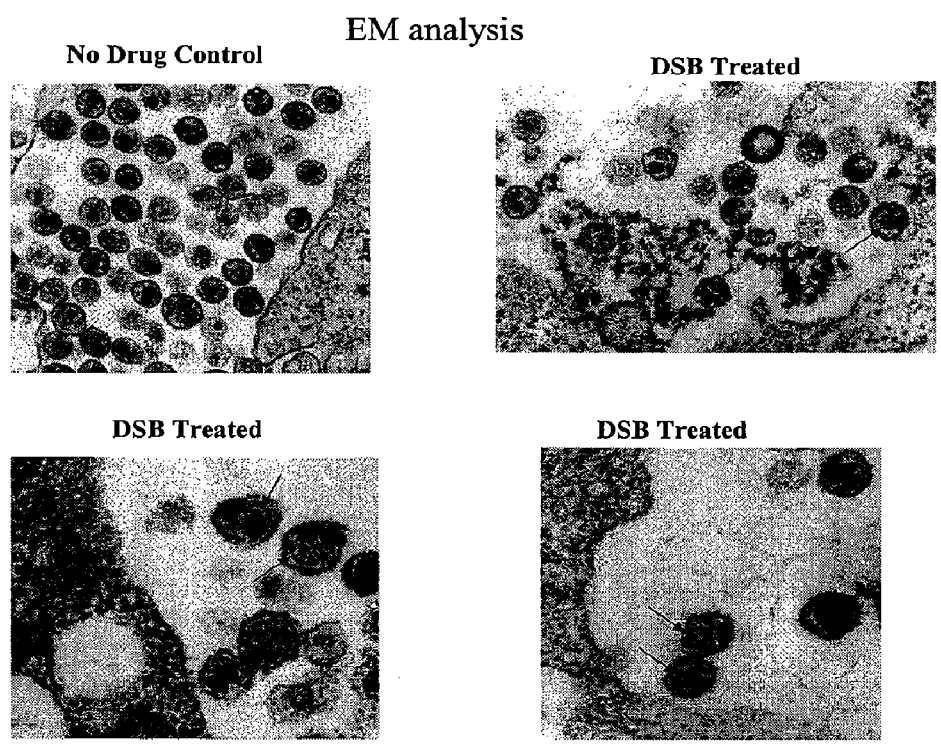

HeLa cells were transfected with HIV-1 infectious molecular clone pNL4-3 and treated as described previously with DSB. Following treatment, DSB-treated infected cells were fixed in glutaraldehyde and analyzed by EM. The results of this analysis are shown in FIG. 3.

These results are consistent with a compound that disrupts p25 to p24 processing which generates non-infectious morphologically aberrant viral particles.

3-O-(3',3'-dimethylsuccinyl) betulinic acid (DSB) is an example of a compound that disrupts p25 to p24 processing and potently inhibits HIV-1 replication. However, this compound does not inhibit PR activity, and its action is specific for the p25 to p24 processing step, not other steps in Gag processing. Furthermore, DSB treatment results in the aberrant HIV particle morphology described above.

Example 7

In vitro selection for HIV-1 isolates resistant to compounds that disrupt the processing of the viral Gag capsid (CA) protein from the CA-spacer peptide 1 protein precursor.

A series of experiments were performed to select for viruses resistant to inhibition by 3-O-(3',3'-dimethylsuccinyl) betulinic acid (DSB), an inhibitor HIV-1 maturation. For each experiment, either NL4-3 or RF virus isolate was used to infect two cell cultures. Following infection, one culture was maintained in growth medium containing DSB, while the other culture was maintained in parallel in growth medium lacking DSB.

In one experiment, H9 cells that had been infected with RF virus were maintained in the presence or absence of increasing concentrations of DSB (0.05-1.6 μg/ml). The cells were passaged every 2-3 days with the addition of fresh drug. Virus replication was monitored by p24 ELISA every 7 days. At that time, DSB-treated cultures with high levels of p24 were passaged by co-cultivation with fresh uninfected H9 cells at a 1:1 ratio of cells in the presence of 1× or 2× the original concentration of DSB. After 8 weeks of co-cultivation, cell-free virus was collected from the culture containing DSB at a concentration of 1.6 μg/ml and used to infect fresh H9 cells. Every 7 days, virus from cultures containing high levels of p24 was passaged by cell-free infection in the presence of 1× or 2× the original concentration of DSB. After 5 weeks of cell-free passaging, virus from the culture containing 3.2 μg/ml DSB was collected and used to infect MT-2 cells. Virus replication in the MT-2 cells, was monitored by observing syncytia formation microscopically. Every 1-3 days, the cells were washed to remove input virus, and fresh drug was added to the culture under selection. Every 3-4 days, following the emergence of extensive syncytia in the culture under selection, supernatant from each culture was collected and passed through a 0.45 μm filter to remove cell debris. This filtered virus supernatant was then used to infect fresh MT-2 cells in the presence or absence of fresh drug. After 4 rounds of cell-free infection (approximately 2 weeks in culture), with the concentration of drug at 3.2 μg/ml, virus stocks were collected and frozen for further analysis.

In a second experiment, a stock of virus derived from the molecular clone pNL4-3 ($5.7\times10^4$ $TCID_{50}$) was used to infect MT-2 cells ($6\times10^6$ cells) and cultures were maintained in the presence or absence of PA-457 at a concentration of 1.6 μg/ml. Every 1-3 days, the cells were washed to remove input virus, and fresh drug was added to the culture under selection. Virus replication was monitored by observing syncytia formation microscopically. Every 3-7 days, following the emergence of extensive syncytia in the culture under selection, supernatant from each culture was collected and passed through a 0.45 μm filter to remove cell debris. This filtered virus supernatant was then used to infect fresh MT-2 cells in the presence or absence of fresh drug. After 5 rounds of cell-free infection, and every other round thereafter, the concentration of drug was doubled. After 10 rounds of cell-free infection (approximately 7 weeks in culture), when the concentration of drug reached 12.8 μg/ml, virus stocks were collected and frozen for further analysis.

Example 8

Characterization of HIV-1 isolates selected for resistance to compounds that disrupt the processing of the viral Gag capsid (CA) protein from the CA-spacer peptide 1 protein precursor.

Virus stocks derived as described above were further analyzed both phenotypically and genotypically to characterize the nature of their drug-resistance. The resistance of the viruses to 3-O-(3',3'-dimethylsuccinyl)-betulinic acid (DSB) was determined in virus replication assays. Briefly, the virus stocks were first titered in H9 cells by quantitating the levels of p24 (by ELISA) in cultures 8 days after infection with serial 4-fold dilutions of virus. Virus input was then normalized for a second assay in which each virus is cultured for 8 days in the presence of serial 4-fold dilutions of drug. The $IC_{50}$ for each virus was determined as the dilution of drug that reduced the p24 endpoint level by 50% as compared to the no-drug control. Two independently derived virus stocks had $IC_{50}$ values greater than 1 μg/ml for DSB, as compared to an $IC_{50}$ of 0.01 μg/ml for virus that had been cultured in parallel in the absence of drug.

To determine if the resistant viruses were able to escape the CA-SP1 cleavage defect caused by DSB in wild-type virus, stocks of each virus grown in either the presence or absence of drug were analyzed by Western blot. Virus was pelleted through a 20% sucrose cushion from filtered culture supernatants that were collected 60 hr post-infection and 18 hr after the cells had been washed and fresh drug added. The viruses were lysed, and the amount of each virus was normalized by quantitating p24 levels in each sample. Western blot analysis of the viral proteins in each sample demonstrated that the drug-resistant viruses did not contain the CA-SP1 product in the presence of DSB, confirming that these viruses were resistant to the effects of the drug on this cleavage event.

Finally, to identify the genetic determinants of DSB resistance, the entire Gag and PR coding regions of the viral genomes were amplified by high-fidelity RT-PCR for sequencing. The viral RNA was purified from each virus lysate prepared as described above and digested with DNase to remove any contaminating DNA. The RT-PCR products were then gel-purified to remove any non-specific PCR products. Finally, both strands of the resulting DNA fragments were sequenced using overlapping a series of primers. Two amino acid mutations were identified that are independently capable of conferring resistance to DSB, an alanine to valine substitution in the Gag polyprotein at residue 364 in the NL4-3 isolate and at residue 366 in the RF isolate. These are the first and the third residues, respectively, downstream of the CA-SP1 cleavage site (the N-terminus of SP1). Alanine is highly conserved at each of these positions throughout all HIV-1 clades in the database. Additional determinants of resistance may be revealed by comparing the sequence of SW, which is resistant to DSB, in the region of its CA-SP1 cleavage site (FIG. 10) to that of HIV-1 and by mutagenesis of the HIV-1 CA-SP1 region.

Having now fully described this invention, it will be understood to those of ordinary skill in the art that the same can be performed within a wide and equivalent range of conditions, formulations and other parameters without affecting the scope of the invention or any embodiment thereof. All patents and publications cited herein are fully incorporated by reference in their entirety.

What is claimed is:

1. A method of treating HIV-1 infection in a patient, comprising:

determining whether the HIV-1 contains a mutation or a substitution of Ala to Val at a position corresponding to residue 364 or 366 of HIV-1 Gag (residue 1 of SP1) as compared to the sequence of either the wild type strain NL4-3 or the wild type strain RF; and administering to a patient in need thereof a compound that inhibits p25 (CA-SP1) processing to p24 (CA) if the HIV-1 does not contain the mutation, wherein said compound is selected form the group consisting of (a) 3-O-(3',3'-dimethylsuccinyl) betulinic acid (DSB), (b) 3-0-(3',3'-dimethylsuccinyl) betulin, (c) 3-O-(3',3'-dimethylglutaryl) betulin, (d) 3-O-(3',3'-dimethylsuccinyl) dihydrobetulinic acid, (e) 3-O-(3',3'-dimethylglutaryl) betulinic acid, (f) (3',3'-dimethylglutaryl) dihydrobetulinic acid, (g) 3-O-diglycolyl-betulinic acid, (h) 3-O-diglycolyl-dihydrobetulinic acid, (i) a pharmaceutically acceptable salt of any of (a)-(h), and (j) combinations thereof.

* * * * *